United States Patent
Bergeron, Jr.

[11] Patent Number: 5,962,533
[45] Date of Patent: *Oct. 5, 1999

[54] HYDROXY POLYAMINES

[75] Inventor: Raymond J. Bergeron, Jr., Gainesville, Fla.

[73] Assignee: University of Florida Research Foundation, Inc., Gainesville, Fla.

[*] Notice: This patent issued on a continued prosecution application filed under 37 CFR 1.53(d), and is subject to the twenty year patent term provisions of 35 U.S.C. 154(a)(2).

[21] Appl. No.: 08/595,877

[22] Filed: Feb. 6, 1996

[51] Int. Cl.$^6$ ............................ A61K 31/13; C07C 215/00
[52] U.S. Cl. .......................... 514/674; 514/669; 514/667; 514/867; 564/503; 564/506
[58] Field of Search .................................. 564/506, 503, 564/367; 514/867, 669, 674, 667

[56] References Cited

U.S. PATENT DOCUMENTS

| | | | |
|---|---|---|---|
| 4,778,813 | 10/1988 | Fenyes et al. | 514/357 |
| 5,393,757 | 2/1995 | Bergeron, Jr. et al. | 514/256 |
| 5,541,230 | 7/1996 | Basu et al. | 564/512 |

FOREIGN PATENT DOCUMENTS 134676  4/1986  Poland .

OTHER PUBLICATIONS

Basu et al., "Effects of variation in the structure of spermine on the association with DNA and the induction of DNA conformational changes". Biochem. J. vol. 269, 329–334, 1990.

Edwards et al., "Synthesis and DNA–binding properties of polyamine analogues". J. Med. Chem. vol. 34, 2414–2420, 1991.

Stein, "Internal Medicine", 4th edition, pp. 699–715, 1995.

*Primary Examiner*—Jose' G. Dees
*Assistant Examiner*—Barbara Badio
*Attorney, Agent, or Firm*—Kerkam, Stowell, Kondracki & Clarke; Dennis P. Clarke

[57] ABSTRACT

Disclosed are polyamines having the formula:

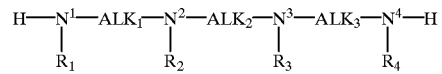

or salts or stereoisomers thereof wherein $R_1$–$R_4$ and $ALK_1$–$ALK_3$ are as defined in the specification. Pharmaceutical compositions and therapeutic methods of treatment utilizing the compounds are also disclosed.

7 Claims, 7 Drawing Sheets

→ DEETHYLATION

96h L1210 GROWTH VS. DEHSPM AND (HO)2DEHSPM CONCENTRATION

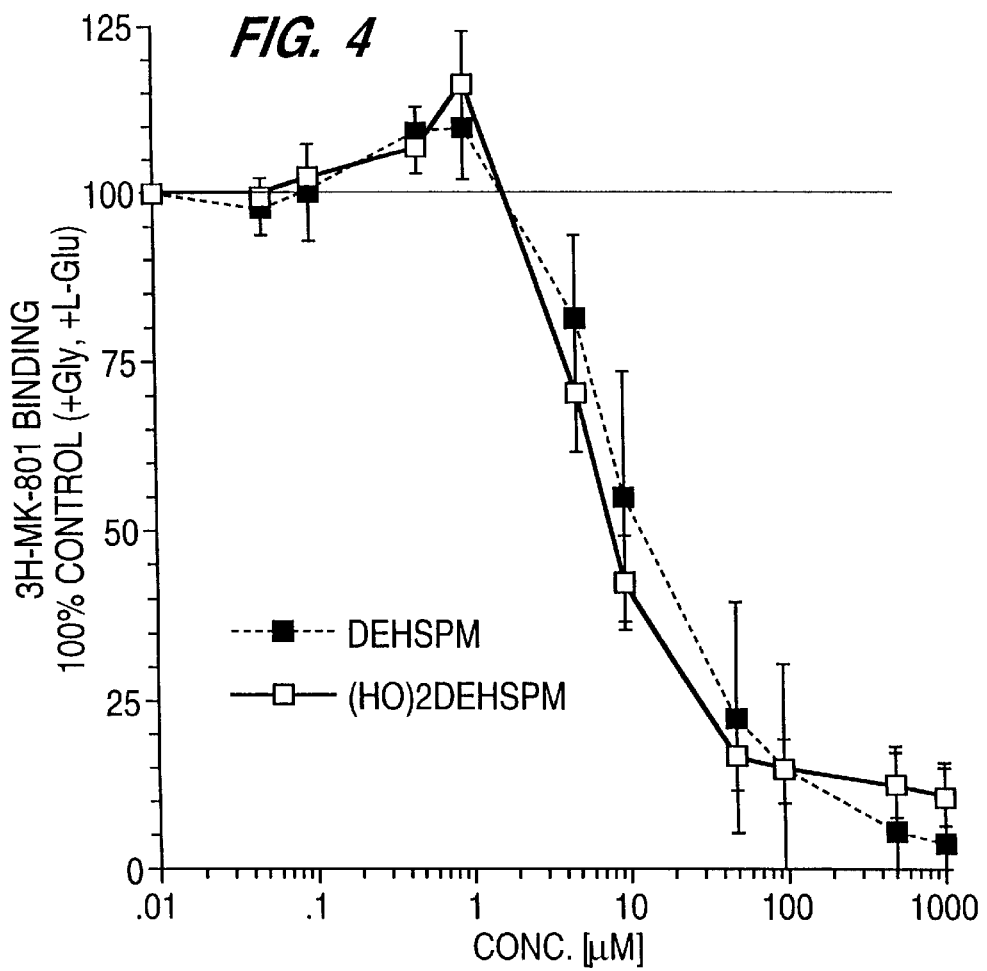
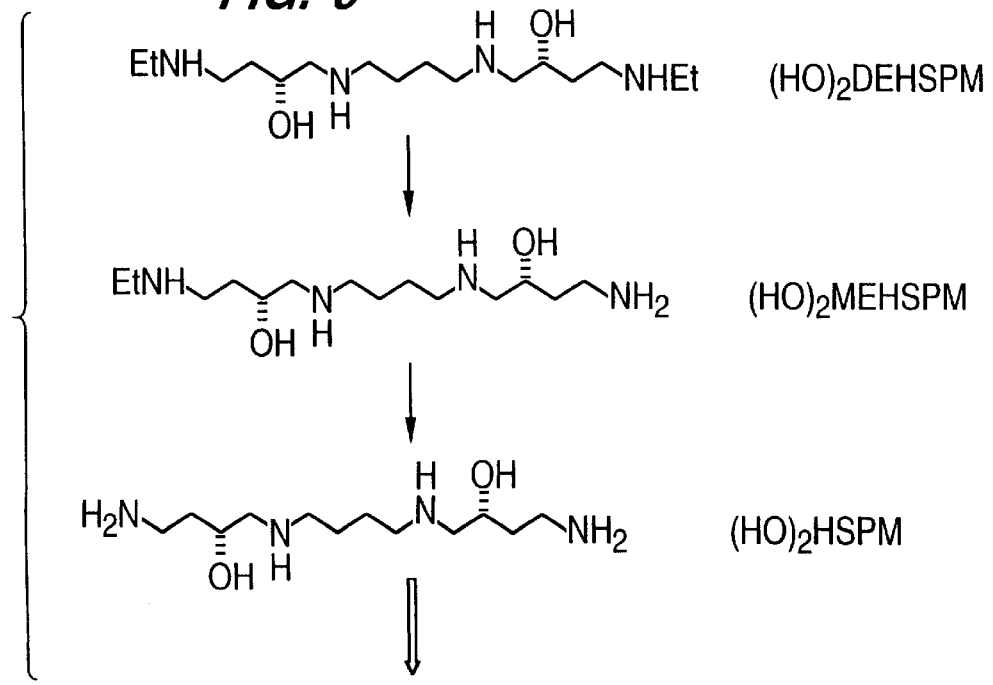

HYDROXY POLYAMINES

BACKGROUND OF THE INVENTION

1. Field of the Invention

The invention relates to novel hydroxy substituted polyamines having valuable therapeutic and other biological properties.

2. Discussion of the Prior Art

In recent years, a great deal of attention has been focussed on the polyamines, e.g., spermidine, norspermidine, homospermidine, 1,4-diaminobutane (putrescine) and spermine. These studies have been largely directed at the biological properties of the polyamines probably because of the role they play in proliferative processes. It was shown early on that the polyamine levels in dividing cells, e.g., cancer cells, are much higher than in resting cells. See Janne et al, *A. Biochim. Biophys. Acta.*, Vol. 473, page 241 (1978); Fillingame et al, *Proc. Natl. Acad. Sci. U.S.A.*, Vol. 72, page 4042 (1975); Metcalf et al, *J. Am. Chem. Soc.*, Vol. 100, page 2551 (1978); Flink et al, *Nature* (London), Vol. 253, page 62 (1975); and Pegg et al, Polyamine Metabolism and Function, *Am. J. Cell. Physiol.*, Vol. 243, pages 212–221 (1982).

Several lines of evidence indicate that polyamines, particularly spermidine, are required for cell proliferation: (i) they are found in greater amounts in growing than in non-growing tissues; (ii) prokaryotic and eukaryotic mutants deficient in polyamine biosynthesis are auxotrophic for polyamines; and (iii) inhibitors specific for polyamine biosynthesis also inhibit cell growth. Despite this evidence, the precise biological role of polyamines in cell proliferation is uncertain. It has been suggested that polyamines, by virtue of their charged nature under physiological conditions and their conformational flexibility, might serve to stabilize macromolecules such as nucleic acids by anion neutralization. See Dkystra et al, *Science*, Vol. 149, page 48 (1965); Russell et al, *Polyamines as Biochemical Markers of Normal and Malignant Growth* (Raven, New York, 1978); Hirschfield et al, *J. Bacteriol.*, Vol. 101, page 725 (1970); Hafner et al, *J. Biol. Chem.*, Vol. 254, page 12419 (1979); Cohn et al, *J. Bacteriol.*, Vol. 134, page 208 (1978); Pohjatipelto et al, *Nature* (London), Vol. 293, page 475 (1981); Mamont et al, *Biochem. Biophys. Res. Commun.*, Vol. 81, page 58 (1978); Bloomfield et al, *Polyamines in Biology and Medicine* (D. R. Morris and L. J. Morton, eds., Dekker, New York, 1981), pages 183–205; Gosule et al, *Nature*, Vol. 259, page 333 (1976); Gabbay et al, *Ann. N.Y. Acad. Sci.*, Vol. 171, page 810 (1970); Suwalsky et al, *J. Mol. Biol.*, Vol. 42, page 363 (1969); and Liquori et al, *J. Mol. Biol.*, Vol. 24, page 113 (1968).

However, regardless of the reason for increased polyamine levels, the phenomenon can be and has been exploited in chemotherapy. See Sjoerdsma et al, *Butterworths Int. Med. Rev.: Clin. Pharmacol. Thera.*, Vol. 35, page 287 (1984); Israel et al, *J. Med. Chem.*, Vol. 16, page 1 (1973); Morris et al, *Polyamines in Biology and Medicine*, Dekker, New York, page 223 (1981); and Wang et al, *Biochem. Biophys. Res. Commun.*, Vol. 94, page 85 (1980).

Because of the role the natural polyamines play in proliferation, a great deal of effort has been invested in the development of polyamine analogues as anti-proliferatives [*Cancer Res.*, Vol. 49, "The role of methylene backbone in the anti-proliferative activity of polyamine analogues on L1210 cells," Bergeron et al, pages 2959–2964 (1989); *J. Med. Chem.*, Vol. 31, "Synthetic polyamine analogues as antineoplastics," Bergeron et al, pages 1183–1190 (1988); *Polyamines in Biochemical and Clinical Research*, "Regulation of polyamine biosynthetic activity by spermidine and spermine—a novel antiproliferative strategy," Porter et al, pages 677–690 (1988); *Cancer Res.*, Vol. 49, "Major increases in spermidine/spermine-$N^1$-acetyl transferase activity by spermine analogues and their relationship to polyamine depletion and growth inhibition in L1210 cells," Basu et al, pages 6226–6231 (1989); *Biochem. J.*, Vol. 267, "Induction of spermidine/spermine $N^1$-acetyltransferase activity in Chinese-hamster ovary cells by $N^1,N^{11}$-bis(ethyl) norspermine and related compounds," Pegg et al, pages 331–338 (1990); *Biochem. J.*, Vol. 268, "Combined regulation of ornithine and S-adenosylmethionine decarboxylases by spermine and the spermine analogue $N^1N^{12}$-bis(ethyl) spermine," Porter et al, pages 207–212 (1990); *Cancer Res.*, Vol. 50, "Effect of $N^1,N^{14}$-bis(ethyl)-homospermine on the growth of U-87 MG and SF-126 on human brain tumor cells," Basu et al, pages 3137–3140 (1990); and *Biochem. Biophys. Res. Commun.*, Vol. 152, "The effect of structural changes in a polyamine backbone on its DNA binding properties," Stewart, pages 1441–1446 (1988)]. These efforts have included the design of new synthetic methods [*J. Org. Chem.*, Vol. 45, "Synthesis of $N^4$-acylated $N^1,N^8$-bis(acyl)spermidines: An approach to the synthesis of siderophores," Bergeron et al, pages 1589–1592 (1980); *Synthesis*, "Reagents for the selective acylation of spermidine, homospermidine and bis-[3-aminopropyl] amine," Bergeron et al, pages 732–733 (1981); *Synthesis*, "Reagents for the selective secondary functionalization of linear triamines," Bergeron et al, pages 689–692 (1982); *Synthesis*, "Amines and polyamines from nitriles," Bergeron et al, pages 782–785 (1984); *J. Org. Chem.*, Vol. 49, "Reagents for the stepwise functionalization of spermidine, homospermidine and bis-[3-aminopropyl]amine," Bergeron et al, page 2997 (1984); *Accts. Chem. Res.*, Vol. 19, "Methods for the selective modification of spermidine and its homologues," Bergeron, pages 105–113 (1986); *Bioorg. Chem.*, Vol. 14, "Hexahydropyrimidines as masked spermidine vectors in drug delivery," Bergeron et al, pages 345–355 (1986); *J. Org. Chem.*, Vol. 53, "Reagents for the stepwise functionalization of spermine," Bergeron et al, pages 3108–3111 (1988); *J. Org. Chem.*, Vol. 52, "Total synthesis of (±)-15-Deoxyspergualin," Bergeron et al, pages 1700–1703 (1987); *J. Org. Chem.*, Vol. 56, "The total synthesis of Alcaligin," Bergeron et al, pages 586–593 (1991); and *CRC Handbook on Microbial Iron Chelates*, "Synthesis of catecholamide and hydroxamate siderophores," Bergeron et al, pages 271–307 (1991)] for the production of these analogues, as well as extensive biochemical studies focussed on the mechanism by which these compounds act [*Cancer Res.*, Vol. 46, "A comparison and characterization of growth inhibition by α-Difluoromethylornithine (DFMO), and inhibitor of ornithine decarboxylase and $N^1,N^8$-bis(ethyl)spermidine (BES), an apparent regulator of the enzyme," Porter et al, pages 6279–6285 (1986); *Cancer Res.*, Vol. 47, "Relative abilities of bis(ethyl) derivatives of putrescine, spermidine and spermine to regulate polyamine biosynthesis and inhibit L1210 leukemia cell growth," Porter et al, pages 2821–2825 (1987); *Cancer Res.*, Vol. 49, "Correlation between the effects of polyamine analogues on DNA conformation and cell growth," Basu et al, pages 5591–5597 (1989); *Cancer Res.*, Vol. 49, "Differential response to treatment with the bis(ethyl)polyamine analogues between human small cell lung carcinoma and undifferentiated large cell lung carcinoma in culture," Casero et al, pages 639–643 (1988); *Mol. Pharm.*, Vol. 39, "Selective cellular depletion of mitochondrial DNA by the polyamine analog, $N^1,N^{12}$-bis(ethyl) spermine, and its relationship to polyamine structure and function," Vertino et al, pages 487–494 (1991); *Biochem. and Biophys. Res. Comm.*, Vol. 157, "Modulation of polyamine biosynthesis and transport by oncogene transfection," Chang et al, pages 264–270 (1988); and *Biopolymers*, Vol. 26, "Structural determinants of spermidine-DNA interactions," Vertino et al, pages 691–703

(1987)]. The mechanistic investigations have encompassed uptake studies, impact on polyamine analogues on polyamine pools and polyamine biosynthetic enzymes, as well as their effects on translational and transcriptional events.

Anti-neoplastic analogues of the naturally occurring polyamines, pharmaceutical compositions and methods of treatment are also disclosed in the following pending patent application Ser. No. 08/231,692 filed Apr. 25, 1994, as well as in U.S. Pat. Nos. 5,091,576 issued Feb. 25, 1992; 5,128,353 issued Jul. 7, 1992; and 5,173,505 issued Dec. 22, 1992. The disclosures of each of the foregoing applications and patents are incorporated herein by reference.

Many of the biologically and pharmacologically valuable polyamines, however, present troublesome metabolic properties in that they are metabolized after administration to the whole animal to potentially toxic metabolites, several of which have a protracted half-life in animals.

Diethylnorspermine (DENSPM) and its metabolites are found in all of the tissues of mice treated with the drug, with the liver and kidney having the highest level of metabolites. These catabolic products included $N^1$-ethylnorspermine (MENSPM), $N^1$-ethylnorspermidine (MENSPD), $N^1$-ethyl-1,3-diaminopropane (MEDAP) and norspermidine (NSPD), suggesting that DENSPM is metabolized (FIG. 1) by (1) N-deethylation and (2) stepwise removal of 3-aminopropyl equivalents by spermine/spermidine $N^1$-acetyl transferase (SSAT)/polyamine oxidase (PAO).

Diethylhomospermine is an example of a polyamine recently found to have potent activity as an anti-neoplastic and anti-diarrheal agent. Its metabolic profile indicates the highest concentration of the polyamine and its principal metabolites, $N^1$-ethylhomospermine (MEHSPM) and homospermine (HSPM), in the liver and kidney. N-deethylation is a key metabolic step in processing DEHSPM (see FIG. 2); however, HSPM does not undergo further metabolism. The accumulation and persistence of HSPM in the tissues of DEHSPM-treated animals is especially striking. Even three weeks after a seven day schedule of DEHSPM, 35% of the drug administered to mice remains in the liver and kidney as drug or metabolites. Interestingly, 90% of the drug remaining in the animal at this time is in the form of HSPM. It is quite clear that the increased chronic toxicity of DEHSPM over $N^1,N^4$-diethylnorspermine (DENSPM) is related to the buildup of HSPM.

The key to a less toxic DEHSPM-like therapeutic agent is one in which the metabolites can be quickly cleared from the tissues. Again, because of the aminobutyl fragments of HSPM, this metabolite cannot be processed through the polyamine biosynthetic network; thus, it remains in the tissues for protracted periods of time. Neither the primary nor the secondary nitrogens of HSPM offer an opportunity for facile conversion to an easily cleared metabolite. Certainly, the methylene backbones cannot be easily oxidized to an excretable metabolite.

It is an object of the present invention to provide novel derivatives of therapeutically and biologically active polyamines which are metabolized to products quickly and easily cleared from animal tissues.

It is another object of the invention to provide novel pharmaceutical compositions and methods of treating human and non-human animals with the novel polyamine derivatives.

SUMMARY OF THE INVENTION

The above and other objects are realized by the present invention, one embodiment of which comprises polyamines having the formula:

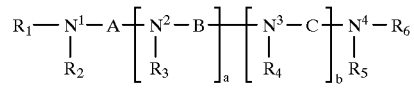

or its possible stereoisomers or a salt thereof with a pharmaceutically acceptable acid wherein:
$R_1$–$R_6$ may be the same or different and are alkyl, aryl, aryl alkyl, cycloalkyl, optionally having an alkyl chain interrupted by at least one etheric oxygen atom, or hydrogen;
$N^1$, $N^2$, $N^3$ and $N^4$ are nitrogen atoms capable of protonation at physiological pH's;
a and b may be the same or different and are integers from 1 to 4;
A, B and C may be the same or different and are bridging groups which effectively maintain the distance between the nitrogen atoms such that the polyamine:
(i) is capable of uptake by a target cell upon administration of the polyamine to a human or non-human animal or is capable of binding to at least one polyamine site of a receptor located within or on the surface of a cell upon administration of the polyamine to a human or non-human animal; and
(ii) upon uptake by the target cell, competitively binds via an electrostatic interaction between the positively charged nitrogen atoms to biological counteranions;
the polyamine, upon binding to the biological counteranion in the cell, functions in a manner biologically different than the intracellular polyamines; and
further wherein at least one of the bridging groups A, B and C contains at least one —CH(OH)— group which is not alpha- to either of the nitrogen atoms.
In the present invention, polyamines with asymmetric centers may occur as racemates, racemic mixtures and as individual enantiomers or diastereoisomers, with all isomeric forms of the compounds being included in the present invention.

An additional embodiment of the invention relates to compositions comprising therapeutically effective amounts of polyamines of the above formula and suitable carriers therefor.

A further embodiment of the invention concerns methods of exerting therapeutic actions on human or non-human animals requiring such action comprising administering thereto therapeutically effective amounts of polyamines of the above formula.

DESCRIPTION OF THE DRAWINGS

FIG. 4 depicts the effects of $(HO)_2$DEHSPM and DEHSPM on the NMDA receptor (MK-801 binding). Each data point represents the mean ±s.d. of three experiments. Each experiment was, in turn, performed in triplicate. "100% activity" is defined as the amount of specific MK-801 binding to washed rat cerebral cortical membranes in the presence of saturating concentrations of coagonists (100 μm L-glutamate, 100 μm glycine) and 2 nm [$^3$H]MK-801.

FIG. 5 depicts the proposed catabolism of $(HO)_2$DEHSPM. The N-deethylation pathway is operative as with DEHSPM; but, in contrast to DEHSPM, the terminal 2-hydroxy-4-aminobutyl segments of $(HO)_2$HSPM are further degraded by other, yet to be characterized, enzymatic systems. Thus, the metabolite $(HO)_2$HSPM does not accumulate.

DETAILED DESCRIPTION OF THE INVENTION

Figure 1:
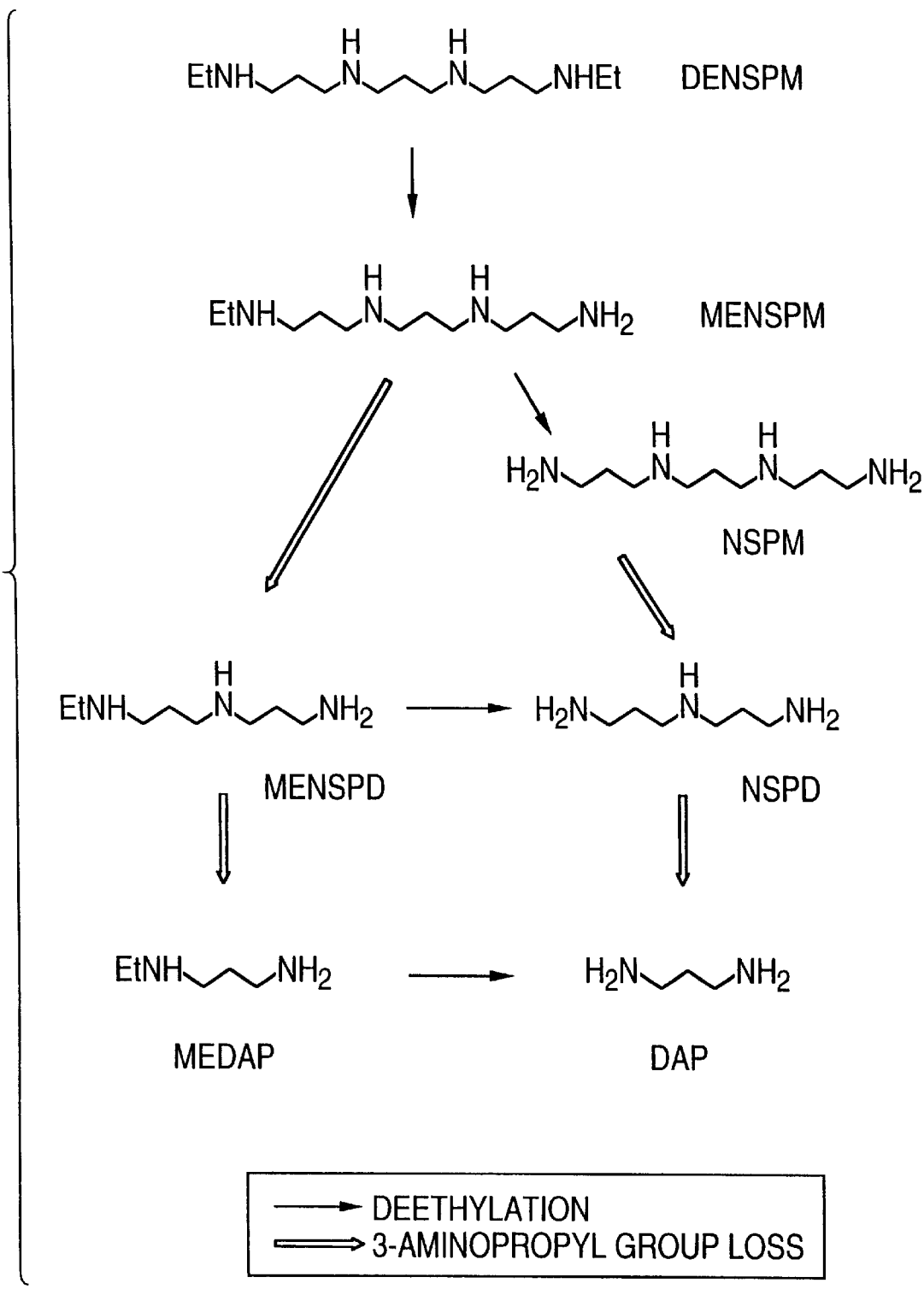
FIG. 1 depicts the metabolic breakdown (catabolism) of DENSPM. Several enzymatic systems are operative: (a) N-deethylation (solid arrows), and (b) de-3-aminopropylation (open arrows) by the constitutive system for catabolism of native polyamines, spermine-spermidine $N^1$-acetyltransferase (SSAT)/polyamine oxidase (PAO). The various permutations of these enzymatic reactions are shown.
Figure 2:
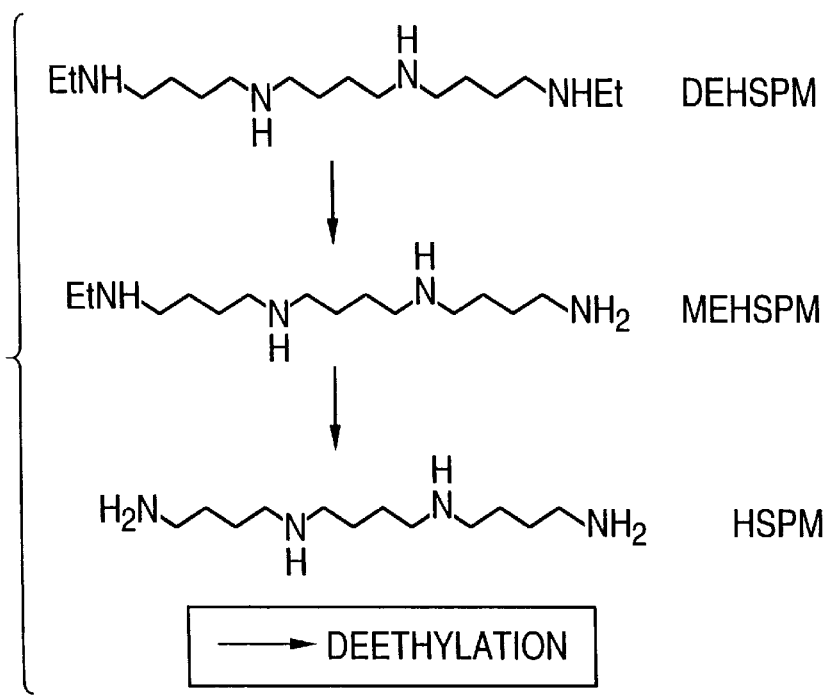
FIG. 2 depicts the catabolism of DEHSPM. Only the N-deethylation pathway is operative; the terminal aminobutyl segments of HSPM are not recognized by SSAT/PAO so that further degradation does not occur.

Efforts undertaken to design polyamine derivatives or analogues which provide metabolic pathways to products which more quickly and easily clear animal tissues, but which are still biologically and therapeutically active, included raising the oxidation state of methylene groups in the polyamines. Employing DEHSPM as an example, it was decided to introduce a single hydroxyl group at each of the external aminobutyl fragments, resulting in $N^1,N^{14}$-diethyl-3,12-dihydroxyhomospermine [$(HO)_2$DEHSPM]. This offered potential sites for either conjugation (e.g., glucuronidation) or further oxidation and clearance of metabolites. SYBYL analysis [SYBYL, Version 6.02, Tripos Associates, Inc., St. Louis, Mo. (Jul. 21, 1993)] of the proposed structure suggested it should behave like DEHSPM at least at the level of competition for the polyamine transport apparatus.

The potential of comparative molecular field analysis (CoMFA) as a predictive tool in identifying analogues which would likely be as biologically successful as the parent compound has been demonstrated. CoMFA is a relatively new technique used to correlate receptor-ligand affinities with the molecular, steric and electrostatic fields presented by the ligands. The output of these studies is an interactive 3D color contour plot from which one can deduce which structural modifications are likely to improve activity. Thus, the approach allows one to predict the activity of new structures which have not been synthesized and are not part of the model data set. Preliminary studies suggest this is a very useful tool in polyamine analogue design. The method has previously been applied to search for quantitative relationships between structures and the ability of the polyamine analogue to compete with spermidine for the polyamine transport apparatus, $K_i$ values. The initial quantitative structure-activity relationship (QSAR) CoMFA included 26 tetraamine analogues and provided a model with a cross-validated $r^2$=0.697 (optimum component 5) and the conventional $R^2$=0.973, F test=152.726, S=0.143. The molecular modeling shows that the relative contribution of the steric and electrostatic term in the QSAR equation are 0.673 and 0.327, respectively, supporting the importance of the geometry of the groups fixed to the nitrogen and of charge.

The library of compounds includes both linear analogues and the cyclic dipiperidyl and dipyridyl compounds, along with $N^1,N^{12}$-bis(2,2,2-trifluoroethyl)spermine (FDESPM). The program was presented with a group of tetraamines in which the nitrogens were both charged and uncharged at physiological pH and was thus able to assess the contribution of charge to $K_i$ data.

TABLE 1

Comparison of Experimental and Predicted $K_i$ Values
of Tetraamine Analogues Using CoMFA Models

| Structure | Abbreviation | $K_i$ ($\mu m$) Actual | $K_i$ ($\mu m$) Calculated |
|---|---|---|---|
| Norspermines | | | |
| 9 | DMNSPM | 5.6 | 5.9 |
| 10 | MENSPM | 7.7 | 7.9 |
| 11 | DENSPM | 17 | 13.2 |
| 12 | DIPNSPM | 40 | 40.7 |
| Spermines | | | |
| 13 | DMSPM | 1.1 | 1.1 |
| 14 | MESPM | 1.7 | 1.1 |
| 15 | DESPM | 1.6 | 2.0 |
| 16 | DPSPM | 2.3 | 2.2 |
| 17 | FDESPM | 285 | 316 |
| Homospermines | | | |
| 18 | DMHSPM | 0.97 | 1.6 |
| 19 | MEHSPM | 1.1 | 1.3 |
| 20 | DEHSPM | 1.4 | 1.9 |
| 21 | DIPHSPM | 8.1 | 8.7 |

TABLE 1-continued

Comparison of Experimental and Predicted $K_i$ Values of Tetraamine Analogues Using CoMFA Models

| Structure | Abbreviation | $K_i$ ($\mu$m) Actual | $K_i$ ($\mu$m) Calculated |
|---|---|---|---|
| 22 | ETBHSPM | 3 | 4.7 |
| 23 | DTBHSPM | 56 | 37.2 |

Homospermine homologues

| Structure | Abbreviation | Actual | Calculated |
|---|---|---|---|
| 24 | DE(3,4,4) | 8 | 3.2 |
| 25 | DE(4,3,4) | 4 | 3.7 |
| 26 | DE(4,5,4) | 6.0 | 5.8 |

Piperidine and Pyridine Derivatives

| Structure | Abbreviation | Actual | Calculated |
|---|---|---|---|
| 27 | PIP(3,4,3) | 60.5 | 69.2 |
| 28 | PYR(3,3,3) | >500 | 426 |
| 29 | PIP(4,4,4) | 4.9 | 4.9 |
| 30 | PYR(4,4,4) | >500 | 562 |
| 31 | PIP(5,4,5) | 18.1 | 17.0 |

Cyclohexane Derivatives

TABLE 1-continued

Comparison of Experimental and Predicted $K_i$ Values of Tetraamine Analogues Using CoMFA Models

| Structure | Abbreviation | $K_i$ ($\mu$m) Actual | Calculated |
|---|---|---|---|
| 32 | BAHSPM | 2 | 3.2 |
| 33 | CHX(4,4,4)-trans | 3.5 | 4.9 |
| 34 | CHX(3,4,3)-trans | 7.9 | 8.3 |

In order to test that the above CoMFA models would be reliable in further drug design, several spermidine analogues (triamines) for which bioassay results were known, but which were not included in the data set of the model, were used for the model verification. The resulting prediction can be compared to the actual activity to gauge the worth of the model. It was quite clear from this study that the model worked well. The biological results from the triamines were then used to further refine the model.

TABLE 2

Comparison of Experimental and Predicated $K_i$ Values of Triamine Analogues Using CoMFA Models

| Structures | Designation | Actual | Calculated |
|---|---|---|---|
| 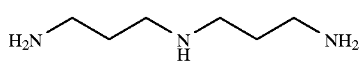 | NSPD | 8.4 | 54.1 |
| 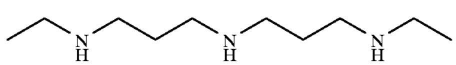 | DENSPD | 200 | 129 |
| 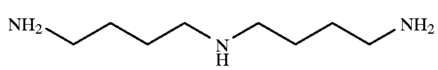 | HSPD | 3.5 | 26.2 |
| 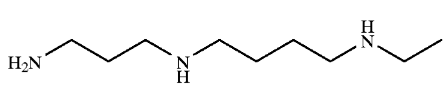 | $N^8$-MESPD | 7.0 | 3.3 |
| 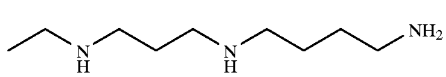 | $N^1$-MESPD | 8.6 | 91.2 |
| 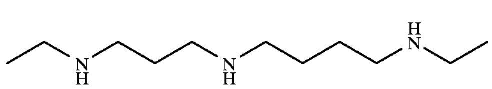 | DESPD | 19.3 | 7.9 |
| 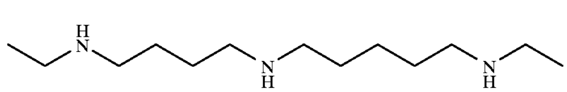 | DEHSPD | 115 | 117 |

The best example of the use of this approach is reflected in its application to the design of (HO)$_2$DEHSPM. Prior to embarking on the synthesis of (HO)$_2$DEHSPM, the computer was "asked" to predict the K$_i$ value. SYBYL suggested that (HO)$_2$DEHSPM should be recognized by the polyamine transport apparatus as effectively as DEHSPM. The agreement between the observed and predicted value was outstanding, i.e., 2.0 v. 1.4 μm.

In this regard, it was elected to assess how effective a K$_i$ prediction would be in projecting the compounds IC$_{50}$ values against, e.g., L1210 cells, its impact on polyamine pools, its effect on the NMDA receptor and its anti-diarrheal activity. A priori one could not anticipate any quantitative relationship between competition for the polyamine transport apparatus and any of these biological properties. However, perhaps it is not unreasonable to expect that if two molecules are recognized by this transport apparatus as being structurally similar, i.e., close in K$_i$ values, it would not be surprising to see that they have similar pharmacological properties in several areas.

Figure 9:
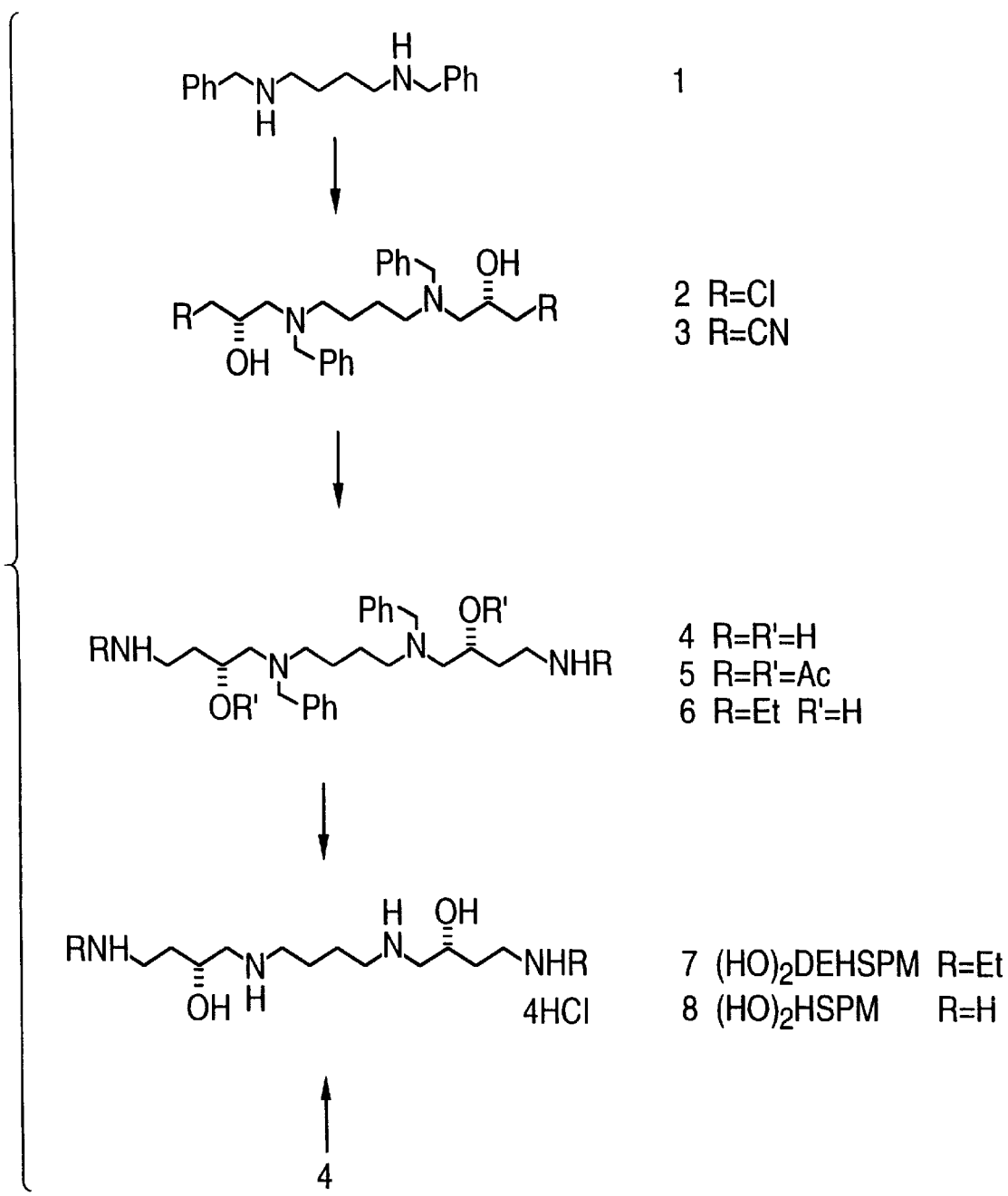
FIG. 9 is a reaction scheme for the synthesis of 3(R),12(R)-dihydroxy-$N^1,N^{14}$-diethylhomospermine [$(HO)_2$DEHSPM] (7) and 4(R),13(R)-dihydroxyhomospermine [$(HO)_2$HSPM] (8).

Referring to FIG. 9, the synthesis of polyamines (HO)$_2$DEHSPM (7) and (HO)$_2$HSPM (8), which contain chiral alcohols on the outer methylene chains, was accomplished by methodology used to prepare hypusine [Bergeron et al, *J. Org. Chem.*, Vol. 58, pages 6804–6806 (1993)]. N,N'-Dibenzylputrescine (1) [Samejima et al, *Chem. Pharm. Bull.*, Vol. 32, pages 3428–3435 (1984)] added regiospecifically to (S)-(+)-epichlorohydrin (2 equiv) to form (S,S)-bischlorohydrin 2. Treatment of 2 with KCN in the presence of 18-crown-6 afforded dinitrile 3 in which the alcohols are now in the (R)-configuration (i.e., diethyl). The cyano groups of 3 were hydrogenated with Raney nickel in methanolic ammonia, resulting in primary α,ω-diamine 4. Hydrogenolysis of the N-benzyl protecting groups of 4 under mild conditions (1 atm, 10% Pd-C, ethanol, 4 equiv HCl) furnished 3(R),12(R)-dihydroxyhomospermine tetrahydrochloride (8). Compound 4 was also exhaustively acylated with acetic anhydride in methylene chloride. Exposure of the resulting 5 to LiAlH$_4$ in THF simultaneously reduced the acetamides to ethyl amines and unmasked the secondary carbinols. Catalytic removal of the benzyl protecting groups of 6 as above afforded terminally diethylated homospermine (R,R) diol 7 as its tetrahydrochloride salt. Substitution of (S)-(+)-epichlorohydrin with (R)-(−)-epichlorohydrin or the racemate would yield the corresponding isomers.

Polyamines of the present invention can possess one or more asymmetric carbon atoms and are thus capable of existing in the form of optical isomers, as well as in the form of racemic or non-racemic mixtures thereof. The optical isomers can be obtained by resolution of the racemic mixtures according to processes known to those skilled in the art, for example, by formation of diastereoisomeric salts by treatment with an optically active acid or base. Examples of appropriate acids are tartaric, diacetyltartaric, dibenzoyltartaric, ditoluoyltartaric and camphorsulfonic acid and the like, followed by separation of the mixture of diastereoisomers by crystallization, then release of the optically active bases from these salts. Another example of a process for separation of optical isomers involves the use of a chiral chromatography column optimally chosen to maximize the separation of the enantiomers. The optically active compounds of the present invention can also be obtained by utilizing optically active starting materials.

BIOLOGICAL STUDIES

Figure 3:
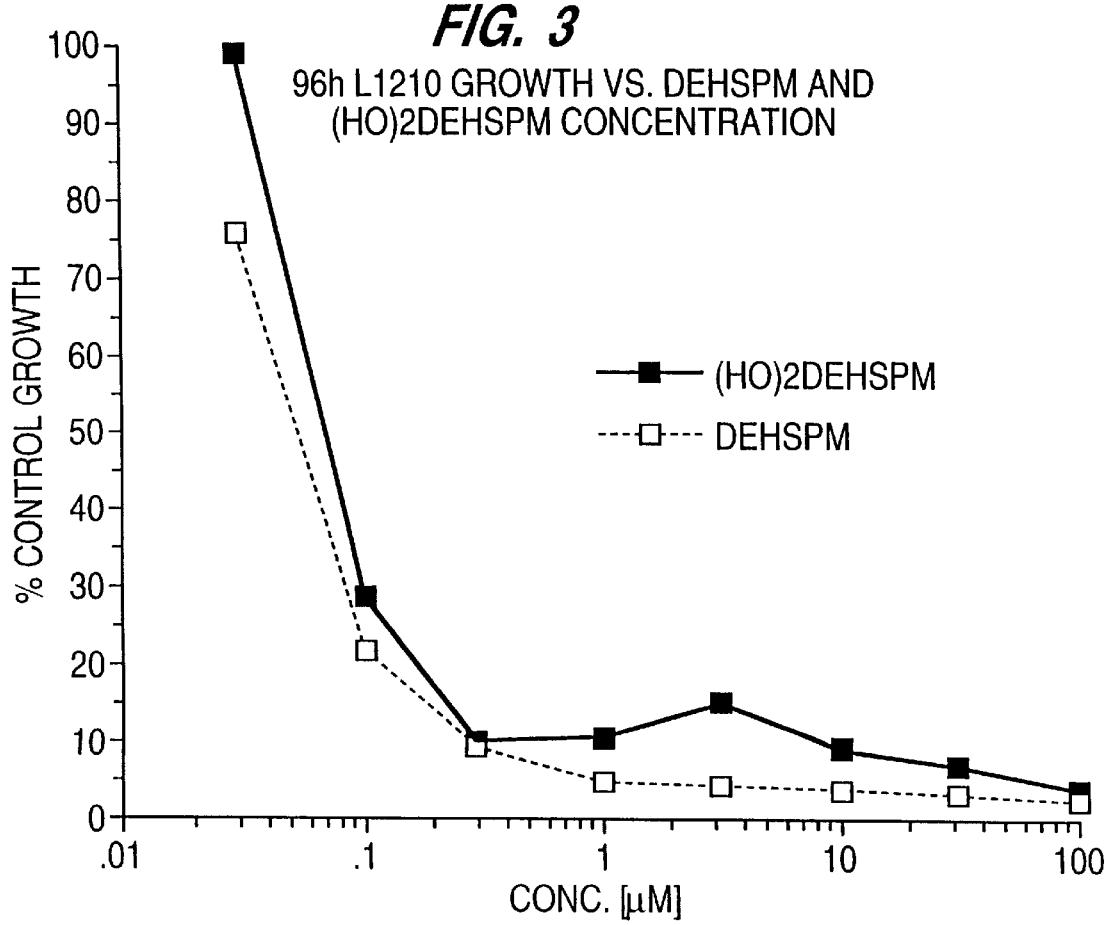
FIG. 3 depicts a comparison of the effects of DEHSPM and $(HO)_2$DEHSPM on L1210 cell 96 hour growth curves. The concentration of drug that results in 50% inhibition of cell growth, i.e., the $IC_{50}$, is between 0.05–0.09 μm for DEHSPM and $(HO)_2$DEHSPM as indicated by the intersection of the "50% growth line" with the respective curves.

IC$_{50}$ Studies. While (HO)$_2$DEHSPM is indeed somewhat more highly substituted than DEHSPM, it nevertheless maintains enough structural similarity to be "read" by L1210 cells as DEHSPM. The 48 and 96 hour IC$_{50}$ values of (HO)$_2$DEHSPM v. DEHSPM are very similar (Table 3). In fact, the actual 48 and 96 hour IC$_{50}$ curves for DEHSPM and (HO)$_2$DEHSPM are nearly identical (FIG. 3).

K$_i$ Studies. The ability of (HO)$_2$DEHSPM and DEHSPM to compete with [$^3$H]-spermidine for uptake into L1210 cells in vitro is very similar, with K$_i$ values of 1.8 and 1.4 μm, respectively.

TABLE 3

Analogue Structures, Acronyms, L1210 Growth Inhibition and Effects on [$^3$H]-Spermidine Transport

| Structure | Abbreviation | IC$_{50}$ (μm) 48 h | IC$_{50}$ (μm) 96 h | K$_i^a$ (μm) |
|---|---|---|---|---|
| (structure) | DEHSPM | 0.2 | 0.07 | 1.4 |
| (structure) | (OH)$_2$-DEHSPM | 0.6 | 0.07 | 1.8 |

$^a$The K$_i$ values were estimated from Lineweaver-Burke plots which showed simply substrate-competitive inhibition of radiolabeled spermidine transport in L1210 cells. The V$_{max}$ was typically about 1 nmol/h-10$^6$ cells.

Polyamine Pools. When L1210 cells were grown in 10 μm DEHSPM (K$_i$=1.4 μm) for 48 hours, they achieved an intracellular concentration of 2.94 mm DEHSPM. At 0.7 μm (HO)$_2$DEHSPM (0.4*K$_i$)for 4 hours, the concentration of intracellular drug reached 1.3 mm, while in 3.5 μm (HO)$_2$DEHSPM (2*K$_i$), intracellular level of analogue reached 2.7 mm, almost identical with the intracellular DEHSPM concentration. At this essentially equimolar intracellular concentration, each analogue had the same impact on polyamine pools. Putrescine and spermidine were depleted to below detectable limits, while spermine was reduced to 60% of control values.

TABLE 4

Impact of Polyamine Analogues on Polyamine Pools[a]

| Compound | Concentration ($\mu$m) | PUT | SPD | SPM | Analogue[b] |
|---|---|---|---|---|---|
| DEHSPM | 10 | 0 | 0 | 61 | 2.94 |
| (OH)$_2$DEHSPM | 0.7 | 45 | 57 | 96 | 1.32 |
|  | 3.5 | 0 | 0 | 68 | 2.73 |

[a]Native polyamine levels in analogue-treated L1210 cells are relative to untreated controls (control = 100%). Typical control values in pmol/10$^6$ L1210 cells are PUT = 192 ± 38; SPD = 2751 ± 163; SPM = 726 ± 34.
[b]Analogue amount is expressed as nmol/10$^6$ cells.

Modulation of [$^3$H]MK-801 binding to the NMDA Receptor by (HO)$_2$DEHSPM. The retention of certain characteristic pharmacological properties of the DEHSPM pharmacophore by (HO)$_2$DEHSPM is clearly demonstrated in FIG. 4. The marked activity of terminally dialkylated tetraamines including DEHSPM on the NMDA receptor and that very small structural changes can result in striking differences in this activity among polyamine analogues had previously been reported [Bergeron et al, *J. Med. Chem.*, Vol. 38, pages 425–428 (1995)]. The dose-effect curves of DEHSPM and (HO)$_2$DEHSPM are virtually superimposable including agonist activity at 0.5–1.0 $\mu$m, but marked antagonist activity at concentrations above 5 $\mu$m with maximal antagonism at concentrations of 50 $\mu$m and above.

Figure 6A:
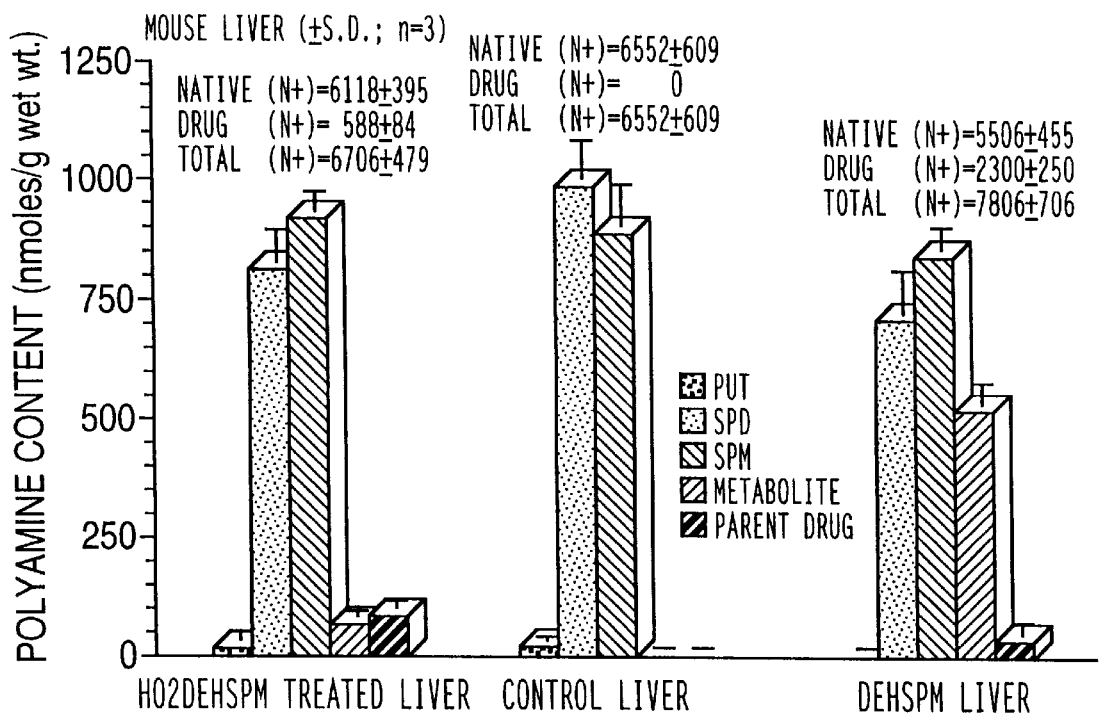
FIG. 6 depicts the quantitation of parent drug $(HO)_2$DEHSPM; dideethylated metabolite, $(HO)_2$HSPM; and native polyamine pools in mouse liver (6a) and kidney (6b). Groups (N=3; ±s.d.) were sacrificed for HPLC analysis 24 hours after cessation of a subchronic dosage regimen (20 mg/kg/day $(HO)_2$DEHSPM as a single intraperitoneal injection daily for five days: total dose=3.0 mg or 6.46 μmol for a 30 g mouse). For comparison, similar data for untreated control and DEHSPM-treated (received "equimolar" subchronic dose of DEHSPM=2.7 mg or 6.25 μmol for a 30 g mouse) mice are plotted. Total polyamine N+ equivalents ±s.d. (n equiv×10−1/g wet weight) are calculated.
Figure 6B:
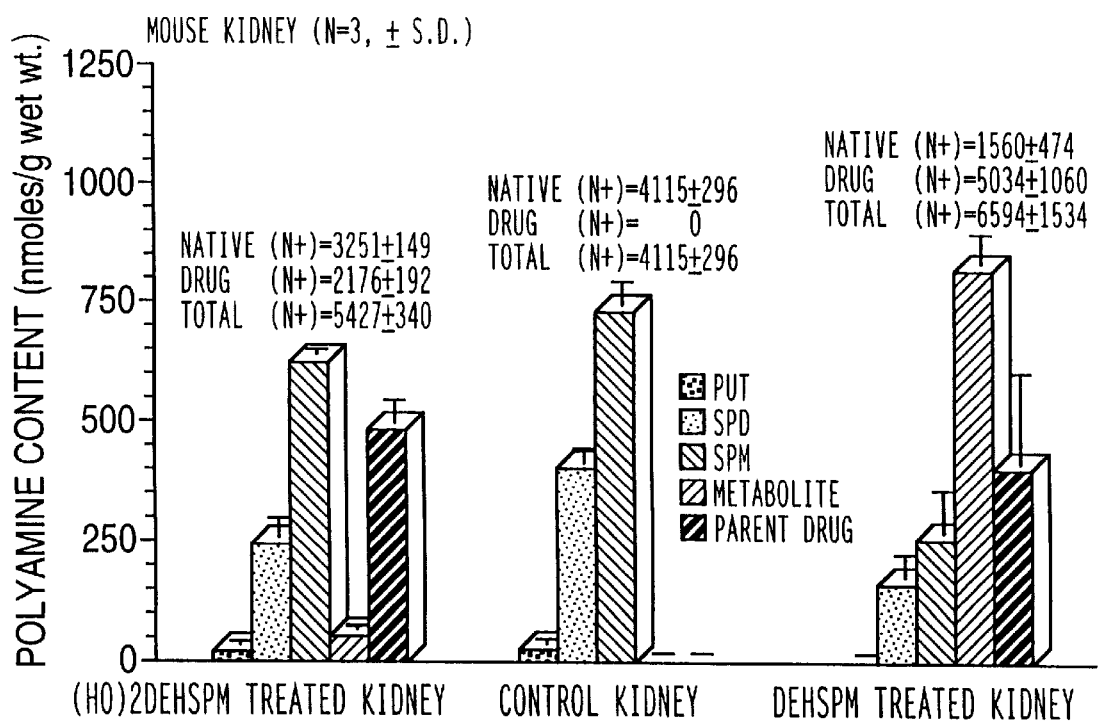

Metabolism of (HO)$_2$DEHSPM v. DEHSPM in Mouse Liver and Kidney. Dansylated samples of authentic (HO)$_2$DEHSPM or (HO)$_2$HSPM resulted in a single fluorescent peak with a molar response similar to that of DEHSPM or HSPM. Dansylation of the HClO$_4$ extracts of (HO)$_2$DEHSPM-treated liver and kidney contained the peaks corresponding to the natural polyamines, PUT, SPD, SPM, as well as unchanged (HO)$_2$DEHSPM. In addition, there was a single additional fluorescent peak with a retention time identical to that of authentic dansylated (HO)$_2$HSPM. It proved impossible to identify a peak in the area in which the dansylated monodeethylated metabolite of (HO)$_2$DEHSPM would be anticipated. However, without an authentic sample of the metabolite, it is not clear that the dansylated monodeethylated metabolite is not buried under other signals. Nevertheless, it is clear that the initial step in liver and kidney one day after cessation of a subchronic equimolar treatment regimen are similar for (HO)$_2$DEHSPM and DEHSPM. In the liver, the level of unchanged drug is similar and low: 83.6±11.7 v. 43.9±12.6 nmol/g wet weight for (HO)$_2$DEHSPM and DEHSPM, respectively (FIG. 6a). Levels in the kidney are also similar, although substantially higher than those in liver: 481±46 [(HO)$_2$DEHSPM] v. 409±178 [DEHSPM] (FIG. 6b). However, there is no substantial accumulation of metabolic products of (HO)$_2$DEHSPM in either tissue. This is in marked contrast with DEHSPM, in which tissues from treated animals contained the dideethylated metabolite HSPM in substantially higher concentrations than the parent drug. Thus, HSPM is present in large quantities in the DEHSPM-treated liver (525±44 nmol/g wet weight) and at even higher levels in the kidneys, where it is easily the most abundant polyamine in the tissue (815±61 nmol/g wet weight), equivalent to all the other polyamines combined. The corresponding dideethylated metabolite (HO)$_2$HSPM is, in contrast, present in both liver (63±2) and kidney (63±9), but in concentrations lower than the parent drug (liver: 84±12; kidney: 481±46).

The lack of accumulation of the dideethylated metabolite from (HO)$_2$DEHSPM is best illustrated in Table 5 which analyzes the data from the perspective of mass balance of the cumulative dose, i.e., how much of the original total dose remains in the liver and kidney and what form is it in, parent drug or metabolite? A 30 g mouse would have received a cumulative dose of 2.7 mg (6.25 $\mu$mol) DEHSPM or 3.0 mg (6.46 $\mu$mol) (HO)$_2$DEHSPM. One day after cessation of treatment, 33.8% (2.11 $\mu$mol) of the original dose of DEHSPM can be accounted for in the liver and kidneys. However, only a small portion, 5.0% or 0.313 $\mu$mol, of the original dose is present in the form of unchanged parent drug; 28.8% or 1.80 $\mu$mol of the total original dose remains in these organs in the form of the dideethylated metabolite, HSPM. HSPM accumulates because it can neither be further metabolized by the polyamine retrograde pathway (SSAT/PAO), nor effectively exported from the cell. In (HO)$_2$DEHSPM-treated animals, a similar amount (6.96% of dose or 0.450 $\mu$mol) of unmetabolized parent drug is present in the liver and kidneys 24 hours after cessation of treatment, but only 3.03% of the original dose is present in the form of the dideethylated metabolite, (HO)$_2$HSPM. In each tissue, the amount of parent drug exceeds the metabolite, reflecting the lack of accumulation of (HO)$_2$HSPM.

TABLE 5

Amount[A] (%) of Total Dose Present in Liver and Kidney as:

|  | Treatment | Unmetabolized Parent Drug DEHSPM/(HO)$_2$DEHSPM | Dideethylated Metabolite HSPM/(HO)$_2$HSPM | Total Drug + Metabolite |
|---|---|---|---|---|
| Liver | DEHSPM[♦] | 0.115 $\mu$mol (1.84 ± 0.53%) | 1.394 $\mu$mol (22.3 ± 2.10%) | 1.509 $\mu$mol (24.15%) |
|  | (HO)$_2$DEHSPM[■] | 0.219 $\mu$mol (3.39 ± 0.48%) | 0.166 $\mu$mol (2.57 ± 0.38%) | 0.385 $\mu$mol (5.96%) |
| Kidneys | DEHSPM[♦] | 0.196 $\mu$mol (3.14 ± 1.37%) | 0.408 $\mu$mol (6.53 ± 0.67%) | 0.604 $\mu$mol (9.67%) |
|  | (HO)$_2$DEHSPM[■] | 0.231 $\mu$mol (.357 ± 0.34%) | 0.030 $\mu$mol (0.47 ± 0.01%) | 0.261 $\mu$mol (4.04%) |
| Both | DEHSPM[♦] | 0.311 $\mu$mol (4.98%) | 1.802 $\mu$mol (28.83%) | 2.113 $\mu$mol (33.82%) |
| Tissues | (HO)$_2$DEHSPM[■] | 0.450 $\mu$mol (6.96%) | 0.196 $\mu$mol (3.03%) | 0.646 $\mu$mol (10.01%) |

[A]Mass balance accounting for fate of the total original dose normalized for 30 g mouse.
[♦]Total Dose = 15 mg/kg per day × 6 days = 90 mg/kg → 2.7 mg (6.25 $\mu$mol) for a 30 g mouse.
[■]Total Dose = 20 mg/kg per day × 5 days = 100 mg/kg → 3.0 mg (6.46 $\mu$mol) for a 30 g mouse.

(HO)$_2$DEHSPM metabolism involves simple deethylation (FIG. 5) as with DEHSPM.

It appears that the initial steps in the tissue distribution and metabolism of (HO)$_2$DEHSPM are indistinguishable from DEHSPM. The levels of unmetabolized drug present in Acute Toxicity. The acute toxicity of (HO)$_2$DEHSPM was assessed after intraperitoneal administration of a single dose of 325 mg/kg to a group of five female CD-1 mice. Three of the five animals died in this experiment, suggesting that the acute toxicity of (HO)$_2$DEHSPM is very similar, if not identical, to that of DEHSPM (LD$_{50}$=325 mg/kg) and DENSPM (LD$_{50}$=325 mg/kg).

Chronic Toxicity. The chronic LD$_{50}$ for DEHSPM was determined to be 38 mg/kg per day×5 days in this study. This value confirms the LD$_{50}$ value previously reported. No deaths were observed in groups of six animals each at (HO)$_2$DEHSPM doses of 20, 40 and 60 mg/kg per day×5 days, so experiments were initiated at higher doses (# deaths/# animals): 70 (0/5); 80 (0/5); 90 (0/10); 100 (1/5); and 120 (2/5) mg/kg per day×5 days. These data indicate an LD$_{40}$ for (HO)$_2$DEHSPM of 120 mg/kg per day×5 days. The LD$_{50}$ was estimated to be 130 mg/kg based on the slope of the toxicity curve. These data establish (HO)$_2$DEHSPM to be at least three times less toxic in a subchronic treatment regimen than its analogue, DEHSPM. While the lower doses of (HO)$_2$DEHSPM did not cause deaths, animals did exhibit signs of toxicity. At 90 mg/kg for five days, the animals all exhibited lethargy, poor coat condition and decreased, ataxic movements. The animals in this (HO)$_2$DEHSPM-treated group lost between 20–30% of their body weight (data not shown), but recovered in a period of twenty days after the dosing regimen. This was in contrast to DEHSPM-treated animals, wherein a 20% loss of body weight is a sign of imminent death. Several severely affected (HO)$_2$DEHSPM-treated animals were necropsied. It was noted that the stomachs of these animals appeared herniated and were extremely distended with food. This suggests that this compound potently blocks gastric transport.

Figure 7A:
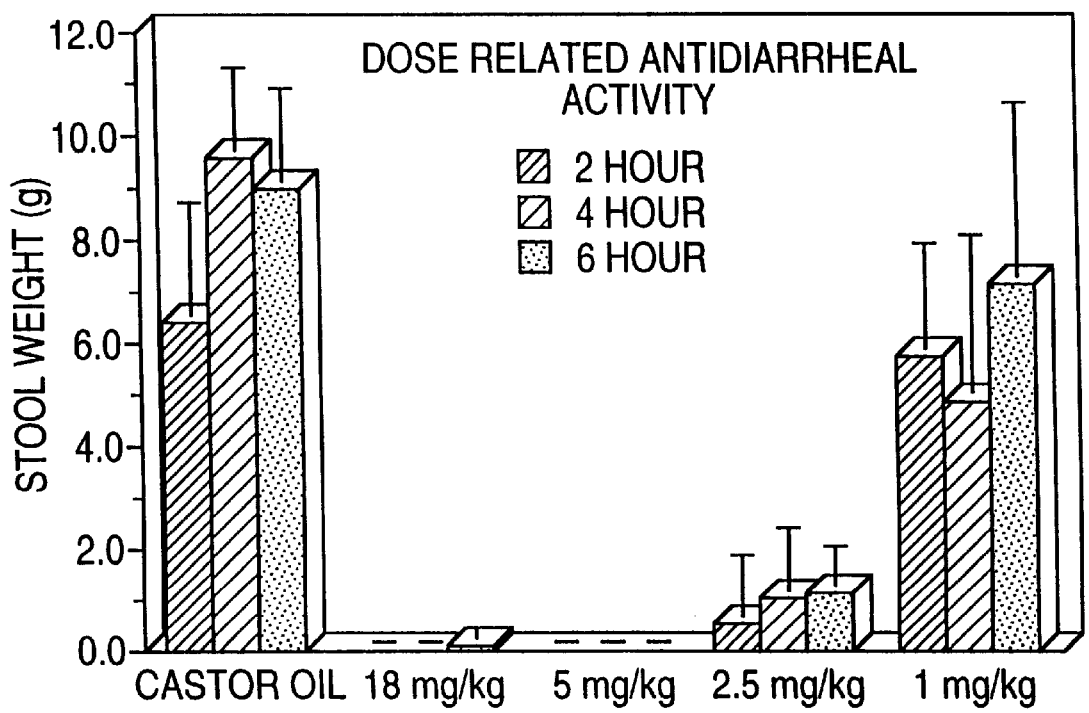
FIG. 7 depicts the anti-diarrheal dose-response for $(HO)_2$DEHSPM in the rat castor oil-induced diarrheal model. Drug was administered as a subcutaneous injection followed, after 30 minutes, by gastric gavage of castor oil (5 ml/kg). Stool output (7a) and body weight loss (7b) were measured at 2, 4 and 6 hours. The minimum effective dose for $(HO)_2$DEHSPM was 5 mg/kg. Data are not corrected for slight evaporative losses that occur during the assay. Such corrections do not significantly affect the results.
Figure 7B:
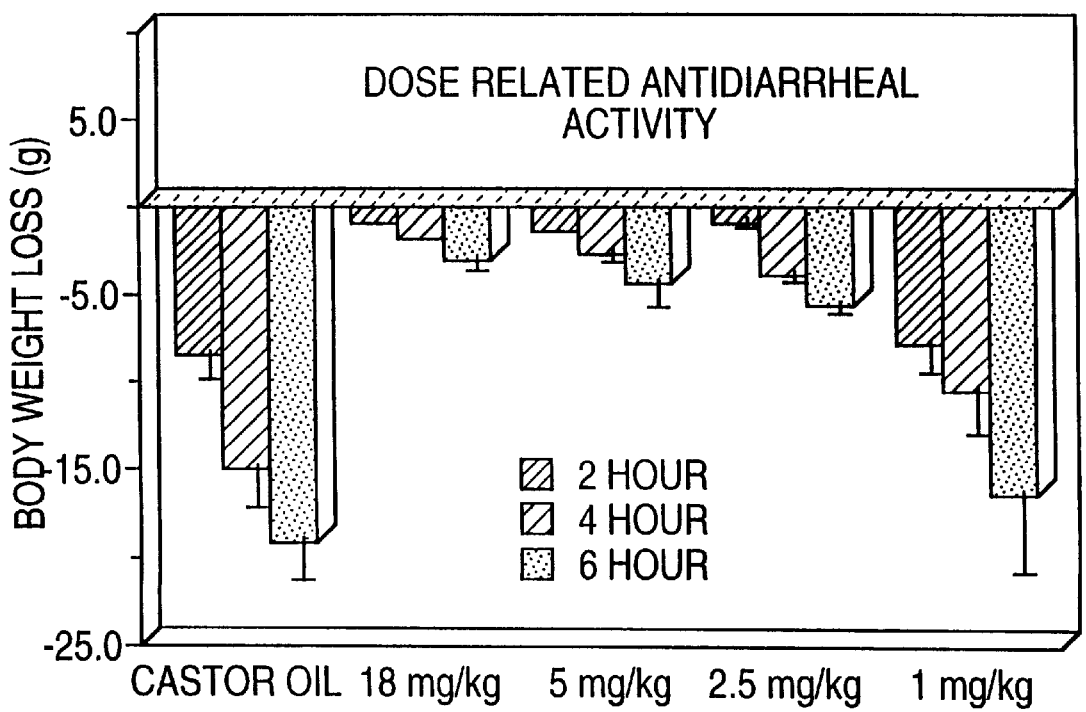

Prevention of Castor Oil-Induced Diarrhea. DEHSPM is an established anti-diarrheal agent in rats and dogs and is currently in Phase 1 clinical trials for the treatment of severe AIDS-related diarrhea (ARD). The dosage of DEHSPM administered to the rats in this study (5 mg/kg) is equivalent to the clinically used dose of 30 mg/m$^2$ in humans. At this dosage, DEHSPM effectively prevented the onset of diarrheal stooling for the six hour time period of the assay in this castor oil-induced diarrheal rat model. At a dose of 5 mg/kg, (HO)$_2$DEHSPM was as effective as DEHSPM at preventing diarrhea. In addition, the body weight loss for each group was very similar. Neither group exhibited any diarrheal stooling during the assay. This suggests that (HO)$_2$DEHSPM could be an effective anti-diarrheal agent for clinical use. The dose-response relationship shows, as expected, the higher dose of 18 kg/mg of (HO)$_2$DEHSPM effectively prevented the onset of diarrhea, but indicated that 5 mg/kg of (HO)$_2$DEHSPM was the minimum effective dose for prevention of diarrhea in this assay. At 2.5 mg/kg, (HO)$_2$DEHSPM was partially effective, resulting in reduced stool output (FIG. 7a) and maintenance of body weight (FIG. 7b), although some diarrhea did occur within the six hour observation period. At 1 mg/kg, (HO)$_2$DEHSPM was not an effective anti-diarrheal agent.

Figure 8A:
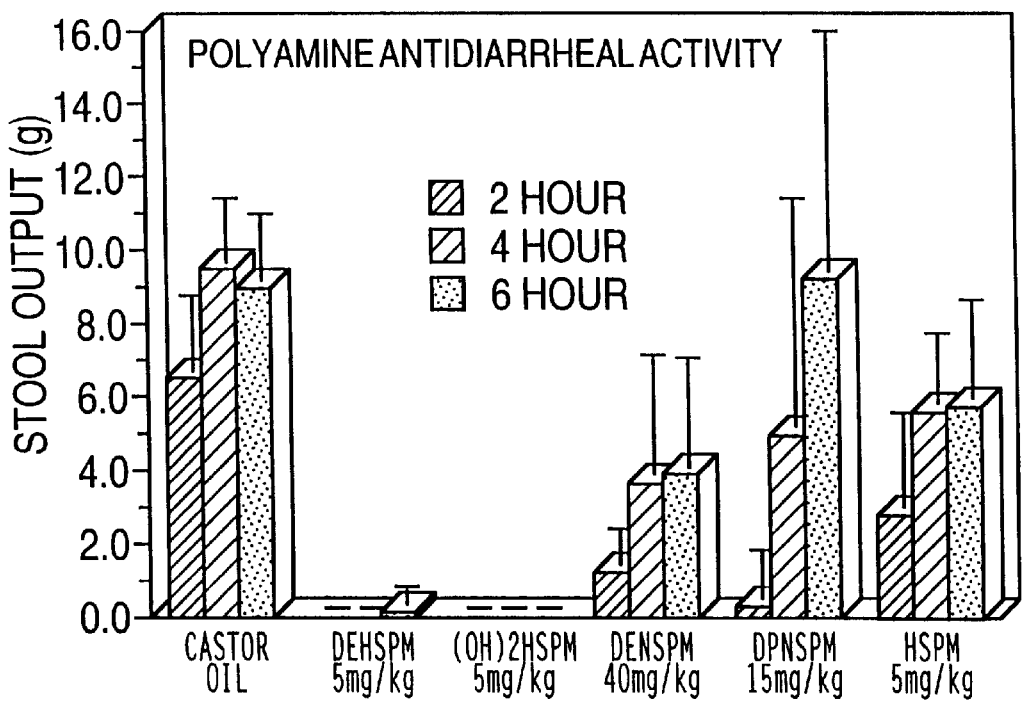
FIG. 8 depicts the anti-diarrheal activity of polyamine analogues DENSPM, DPNSPM, HSPM, DEHSPM and $(HO)_2$DEHSPM. All drugs were administered as a subcutaneous injection followed, after 30 minutes, by gastric gavage of castor oil (5 ml/kg). Stool output (8a) and body weight loss (8b) were measured at 2, 4 and 6 hours. Both DEHSPM and $(HO)_2$DEHSPM-treated rats showed virtually no stool output and lost little of their body weight as compared to castor oil control rats. HSPM, DPNSPM and DENSPM-treated rats all became diarrheal during the 6 hour assay. Data are not corrected for slight evaporative losses that occur during the assay. Such corrections do not significantly affect the results.
Figure 8B:
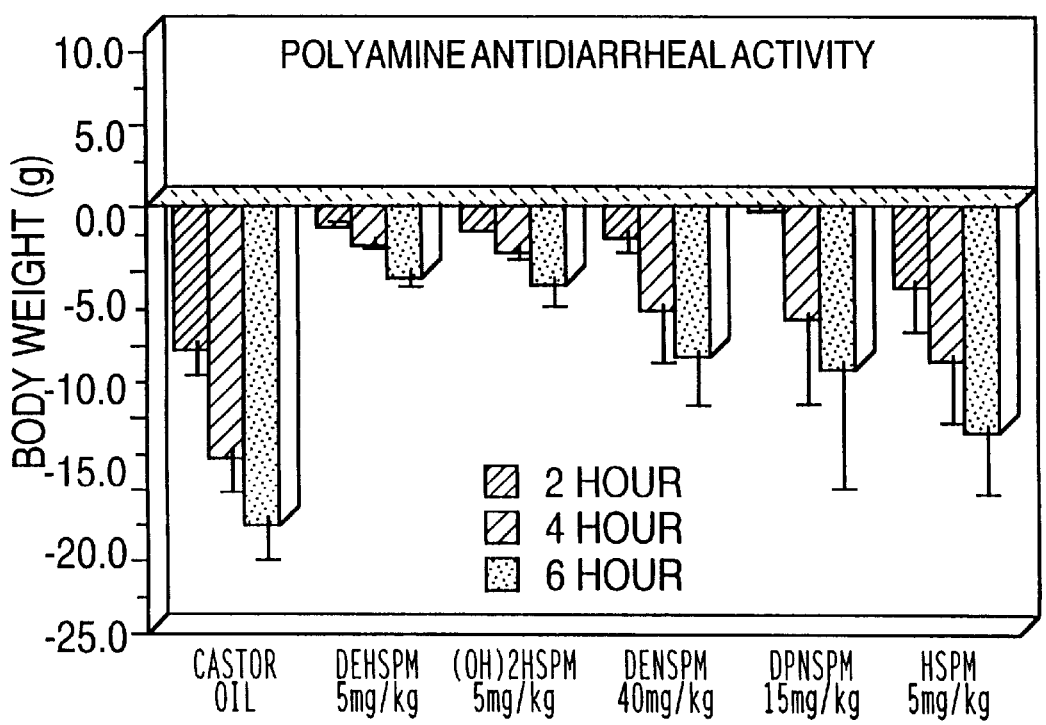

Although the onset of diarrhea was slightly delayed relative to control rats and the total weight of stool output was somewhat less, the norspermine analogues, DENSPM and DPNSPM, even at doses of 40 and 15 mg/kg, respectively, were far less active than the homospermine compounds. Data for both stool output (FIG. 8a) and weight loss (FIG. 8b) clearly illustrate the similarity between DEHSPM and (HO)$_2$DEHSPM and their differences from DENSPM, DPNSPM and HSPM.

While (HO)$_2$DEHSPM is indeed more highly substituted than DEHSPM, it nevertheless maintains enough structural similarity to DEHSPM to be "read" by L1210 cells as DEHSPM. First, the abilities of (HO)$_2$DEHSPM and DEHSPM to compete with radiolabeled spermidine for transport into L1210 cells were found to be essentially identical, just as computer-assisted molecular modeling had predicted. HPLC analysis of L1210 cells grown for 48 hours in the presence of analogue concentrations ranging from 0.4*K$_i$ to 4*K$_i$ suggested a concentration dependent accumulation of analogue which appeared to reach saturation at an intracellular concentration of ca. 3 mm. At this intracellular concentration, each analogue had a very similar effect on intracellular native polyamine pools. Finally, (HO)$_2$DEHSPM and DEHSPM have the same effect on L1210 cell growth, with nearly identical 48 and 96 hour dose-effect curves.

Tetraamines are only poorly exported from cells unless acetylated and the cytosolic acetylase, SSAT, only recognizes aminopropyl moieties with a primary amino terminus as substrates. Thus, the first requirement to enable metabolic clearance of terminal diethyltetraamine analogues is N-deethylation to provide a primary amine terminus. It is interesting to note that under in vitro conditions, L1210 cells apparently do not N-deethylate either (HO)$_2$DEHSPM or DEHSPM to any significant extent. In contrast, tissues examined from animals (mouse, rat, dog) treated with DENSPM or DEHSPM do contain N-deethylated metabolites, thus meeting the first requirement of SSAT for a primary amine terminus. However, if the second criterion of an exposed aminopropyl segment is not met, further degradation via the SSAT/PAO pathway is precluded. Thus, HSPM, a tetraamine comprised exclusively of aminobutyl segments, can neither be further degraded nor exported from the cell, resulting in its accumulation. It was postulated that this accumulation and persistent retention of HSPM was responsible for the markedly greater toxicity (4–5 fold) of DEHSPM v. DENSPM when administered chronically, even though the acute toxicities of DENSPM and DEHSPM are essentially identical. Therefore, the design concept was to modify the polyamine backbone of DEHSPM in such a manner as to render the aminobutyl segments susceptible to further metabolic transformation and clearance.

It was elected to introduce hydroxy groups into the external aminobutyl segments of DEHSPM in a position and configuration analogous to the (R)-(−)-2-hydroxyputrescine segment of hypusine. The rat liver is able to convert 2-hydroxyputrescine itself to γ-amino-β-hydroxybutyric acid. Thus, it was hoped that enzymes involved in 2-hydroxyputrescine and/or hypusine metabolism or perhaps other enzyme systems present in normal tissues might be able to degrade or otherwise facilitate elimination of the tetraamine. Possibilities could include, for example, (1) direct conjugation of the OH to make the molecule exportable and excretable, e.g., glucuronidation; or (2) oxidation at the hydroxyl-bearing carbon either by (a) a constitutive enzyme system normally functioning in hypusine metabolism, or (b) by some other more "non-specific" oxidase/dehydrogenase to result in cleavage of the external aminobutyl segments. While there is as yet no evidence as to which of these or other degradative mechanisms is operating, it is clear that there is no significant accumulation of metabolic product(s) that form polydansyl fluorescent derivatives under assay conditions, e.g., (HO)$_2$HSPM, which explains the threefold decrease in chronic toxicity of (HO)$_2$DEHSPM compared to DEHSPM. These results support the view that the degree of tetraamine buildup and its duration are responsible for a substantial portion of the toxicity that can occur with DEHSPM and validate the hydroxylated polyamine analogue design concept.

The data clearly support earlier findings that the critical issue in how the cell "reads" a polyamine analogue is very dependent on the molecule's charge and the separation between the charge centers [Bergeron et al, *J. Med. Chem.*, Vol. 38, pages 2278–2285 (1995)]. Thus, it is possible to operate on the methylene backbones of these molecules, the insulators between charged centers, altering their metabolic properties while still maintaining the desired pharmacological activity. As has been demonstrated, such metabolic programming can result in polyamine analogues with substantially reduced toxicities. Finally, it seems clear that the CoMFA profiles generated from an expanding library of polyamines are very useful in drug design by assessing whether or not a cell will recognize modified analogues, at least at the level of polyamine transport. These modifications in the backbone can be made while still maintaining the desired pharmacological properties.

EXAMPLES

In the following examples, chemical reagents were purchased from Aldrich Chemical Company. Reactions using hydride reagents were run in distilled DMF under a nitrogen atmosphere. THF was distilled from sodium and benzophenone. Fisher Optima grade solvents were routinely used and organic extracts were dried with sodium sulfate. Silica gel 32–63 (40 $\mu$m "flash") from Selecto, Inc. (Kennesaw, Ga.) was used for column chromatography. Melting points were determined on a Fisher-Johns melting point apparatus and are uncorrected. Proton NMR spectra were run at 300 MHz in $CDCl_3$ (not indicated) or $D_2O$ with chemical shifts given in parts per million downfield from tetramethylsilane or 3-(trimethylsilyl)propionic-2,2,3,3-$d_4$ acid, sodium salt, respectively. Coupling constants (J) are in hertz. FAB mass spectra were run in a m-nitrobenzyl alcohol matrix. Elemental analyses were performed by Atlantic Microlabs, Norcross, Ga.

Computer Modeling. A series of N-alkylated polyamines, terminally dialkylated analogues and homologues of spermine were used to generate the CoMFA. The structures and the $K_i$ values of these polyamine analogues, which have been synthesized by methods developed by Bergeron et al [*J. Med. Chem.*, Vol. 37, pages 3464–3476 (1994); ibid, Vol. 38, pages 2278–2285 (1995); ibid, Vol. 31, pages 1183–1190 (1988)], are listed in Table 1 above.

All of the compounds were screened for their 48 and 96 hour $IC_{50}$ values in L1210 cell culture assays. The same cell line was utilized to evaluate the tetraamines's competition with radiolabeled spermidine for the polyamine uptake apparatus ($K_i$). The $K_i$ values here are the concentrations of drugs required to inhibit the uptake of radioactive spermidine transport by 50% (Table 1).

On the basis of pKa values measured for DENSPM (11), DESPM (15), FDESPM (17), DEHSPM (20), PIP(4,4,4) (29), PYR(4,4,4) (30) and PIP(5,4,5) (31) (Table 1), the following reasonable assumptions have been made about the protonation state. All of the non-aromatic, non-trifluoroethylated tetraamines are largely in the form of the tetracation at the physiological pH of 7.2. The spermine analogues (13–16 and 34) and the homospermine analogues and homologues (18–26, 29 and 31–33) should be 85 and 97%, respectively, in the form of the tetracations. The norspermine analogues (9–12) should be at least 74% in the form of the tetracations. Compounds 17 and 30 should be almost exclusively in the form of the internal dication at physiological pH. Compound 28 should also be a dication, but because of the resonance, it should be a terminal dication. Thus, the calculation of atomic charges and conformational search of these analogues were carried out based on the anticipated protonated structures.

The low energy conformations of polyamine analogues were obtained by systematic conformational searching supported by Tripos Associates, Inc., in SYBYL 6.02 molecular modeling program. The comparative molecular field analyses (CoMFA) were performed using the QSAR option of SYBYL 6.02 program running on a Silicon Graphics with an Indigo2 workstation.

The energies of steric and electrostatic interaction between each of the analogues were calculated as parameters, and a probe atom was placed at the various intersections of regular three-dimensional lattice, large enough to include all of the analogues in the database, and with a 2.0 Å lattice space. The probe atom had the shape of $sp^3$ carbon and a charge of +1.0. The Van der Walls values were taken from the standard Tripos force field, and the atomic charges were calculated by the method of Gasteiger and Marsili [Tetrahedron, Vol. 36, pages 3219–3228 (1980)]. Wherever the probe atom experiences a steric repulsion greater than "cutoff" (30 kcal/mol in these studies), the steric interaction is set to the value "cutoff," and the electrostatic interaction was set to the mean of the other molecular electrostatic interactions at the same location. The resulting steric and electrostatic field values, on a regularly spaced lattice around the analogues, were then correlated with the $K_i$ data for the polyamine transport system for a very efficient statistical method, PLS [Cramer et al, *Quant. Struct. Act. Relat. Pharmacol. Chem. Biol.*, Vol. 7, pages 18–25 (1988)]. Statistical techniques, bootstrapping and cross-validation are used to determine the quality of the correlation. The crossvalidation technique involves random elimination of one or more analogues from the original data set with subsequent equation development and activity prediction for the eliminated analogues in an interactive manner, thus yielding a QSAR equation that is generally of greater predictive value than that derived from conventional regression analysis. The implementation of PLS also rotates the PLS solution back into the original data space, thus generating a "conventional" QSAR equation showing r-square, F test and the standard error S.

The initial alignment of the molecules, the positioning of a molecular model within the fixed lattice, is by far the most critical step in developing a successful CoMFA model since the relative interaction energies depend strongly on relative molecular positions. In this series of molecules, both the end nitrogen atoms of the analogues and the third nitrogen atom were finally found as atom pairs between two molecules for performing a best fit, then followed again by energy-minimization using the standard Tripos force field option, and the resulting structures were used to generate the CoMFA. DESPM was chosen as the template in the alignment of polyamine analogues.

Cell Culture. Murine L1210 leukemia cells were maintained in logarithmic growth as a suspension culture in RPMI-1640 medium containing 10% NuSerum (Collaborative Research, Bedford, Mass.), 2% HEPES-MOPS buffer and 1 mm aminoguanidine (Sigma) at 37° C. in a water jacketed 5% $CO_2$ incubator.

$IC_{50}$ Determinations. Cells were grown in 25 $cm^2$ tissue culture flasks in a total volume of 10 ml. Cultures were treated while in logarithmic growth (0.5–1.0×$10^5$ cells/ml) with the polyamine derivative diluted in sterile water and filtered through a 0.2 $\mu$m filter. Following a 48 hour period, cells were reseeded and incubated for an additional 48 hours.

After the indicated time periods, cells were removed from the incubator for counting. Cell number was determined by electronic particle counting (Model $Z_F$ coulter counter, Coulter Electronics, Hialeah, Fla.) and confirmed periodically with hemocytometer measurements.

The percentage of control growth was determined as follows:

$$\% \text{ of control growth} = \left( \frac{\text{final treated cell no.} - \text{initial inoculum}}{\text{final untreated cell no.} - \text{initial inoculum}} \right) \times 100$$

The $IC_{50}$ is defined as the concentration of compound necessary to reduce cell growth to 50% of control growth after defined intervals of exposure.

Polyamine Pool Analysis. While in logarithmic growth, cells were treated with the polyamine derivatives. At the end of the treatment period, cell suspensions were sampled, washed twice in cold medium RPMI-1640 and pelleted for extraction using 0.6N perchloric acid [Bergeron et al, *Cancer Res.*, Vol. 49, pages 2959–2964 (1989)]. Each supernatant was frozen at −20° C. until analysis by HPLC.

Uptake Determinations. The polyamine derivatives were studied for their ability to compete with [$^3$H]SPD or [$^{14}$C] SPD for uptake into L1210 leukemia cells in vitro. Cell suspensions were incubated in 1 ml of RPMI-1640 containing 1, 2, 4, 6, 8 and 10 μm radiolabeled SPD alone or with the additional presence of 10, 25 and 50 μm polyamine analogue for 20 minutes at 37° C. At the end of the incubation period, tubes were centrifuged at 900 g for 5 minutes at 0–4° C. The pellet was washed twice with 5 ml of cold RPMI-1640 containing 1 mm SPD, dissolved in 200 μl of 1N NaOH at 60° C. for 1 hour, and neutralized with 1N HCl. The material was transferred to a vial for scintillation counting. Lineweaver-Burke plots indicated a simple competitive inhibition with respect to SPD.

NMDA Assay. The procedure for measuring specific binding of [$^3$H]MK-801 to the N-methyl-D-aspartate receptor complex was a modification of the method of Ransom and Stec [*J. Neurochem.*, Vol. 51, pages 830–836 (1988)]. Cerebral cortices from young male Sprague-Dawley rats (200–300 g) were homogenized with 10 volumes ice-cold 0.32M sucrose using a motor-driven glass/Teflon homogenizer. The homogenate was centrifuged at 1,000 g for 10 minutes and the pellet was discarded. The supernatant was then centrifuged at 18,000 g for 20 minutes. The 18,000 g pellet was then resuspended in 10 volumes buffer A (5 mm Tris-HCl, pH 7.7) at 4° C., homogenized using high-intensity ultrasound and centrifuged at 8,000 for 20 minutes. The supernatant and upper buffy coat of the pellet were combined and centrifuged at 50,000 g for 20 minutes. The pellet was then resuspended in 10 volumes buffer A and homogenized using high-intensity ultrasound. These resuspended membranes were then centrifuged at 50,000 g, discarding the supernatant. The membranes were washed in this manner an additional three times and stored as a frozen suspension at −80° C. for at least 18 hours, but no longer than 2 weeks before use.

For binding experiments, frozen membranes were thawed, pelleted at 50,000 g for 20 minutes and washed as described above, except that 20 volumes of buffer A were used for resuspension, for a total of four times. The final pellet was resuspended in buffer B (5 mm Tris-HCl, pH 7.5) at 23° C. The binding assay mixture was 1.00 ml buffer B containing 200–300 μg membrane protein, 100 μm L-glutamate, 100 μm glycine, 2 nm [$^3$H]MK-801 and tetraamine at the following concentrations: 0 ("100%+L-glu,+ gly-Control") and 0.05, 0.1, 0.5, 1, 5, 10, 50, 100, 500 and 1,000 μm. Non-specific binding was determined using 100 μm MK-801.

Binding assays were performed in triplicate at 23° C. for one hour and were terminated by filtration through Whatman GF/B glass fiber filters followed by three 4.0 ml rinses of ice-cold buffer B using a Brandel M-48 Cell Harvester.

Metabolism of (HO)$_2$DEHSPM v. DEHSPM in Mouse Liver and Kidney. Groups of three female CD-1 mice received a subchronic treatment regimen of either (a) (HO)$_2$DEHSPM 20 mg/kg per day intraperitoneally×5 days for a total dose of 100 mg/kg (216 mol/kg); or (b) DEHSPM 15 mg/kg per day intraperitoneally×6 days for a total dose of 90 mg/kg 9208 μmol/kg). In ease case, animals were sacrificed for HPLC analysis one day after the final dose.

HPLC Analysis of Polyamines. Various tissues including the liver and kidney were prepared for HPLC analysis of polyamine content. In order to facilitate their handling, the organs were submerged in liquid nitrogen. Once frozen and weighed, the tissues were homogenized (Tissuemizer, Tekmar, Cincinnati, Ohio) in 1.2N perchloric acid (containing 1,7-diaminoheptane internal standard) in a 1:20 (w/v) ratio. The tissue homogenates were then freeze-thawed three times and stored in a −70° C. freezer until HPLC analysis was performed.

Each chromatographic assay included calibration standards which were treated in the same manner as the samples. The calibration standards (typical retention times in minutes are indicated) were prepared by adding known amounts of PUT (9.63), 1,6-diaminohexane (13.04), 1,7-diaminoheptane (15.39), SPD (20.88), (HO)$_2$HSPM (24.28), SPM (26.75), HSPM (27.60), (HO)$_2$DEHSPM (28.37), MEHSPM (29.80) and DEHSPM (31.85) to a matrix that resembled the sample matrix. The concentration of each polyamine was calculated from the peak area by calibration curves obtained by non-weighted least squares linear regression. Peak area and linear regression calculations were performed on a Macintosh Centris 650 with Rainin Dynamax HPLC Method Manager software (Rainin Instrument Co., Ridgefield, N.J.). The method has a detection limit of 1 nmol/ml and was reproducible and linear over a range of 1 nmol/ml to 100 nmol/ml.

Acute and Chronic Toxicity of DEHSPM and its Metabolites in Mice. For acute toxicities, the polyamine analogues were administered as a single intraperitoneal injection. The animals were scored 2 hours after administration of the drug. All animals were observed for a period of 10 days after the treatment.

In the chronic toxicity regimen, mice were administered the polyamine analogue as one dose per day for five days. Appetite, weight and overall physical appearance were recorded at the time of each injection. After the treatment regimen had been completed, the animals were observed an additional 10 days. The chronic toxicity dosing regimen was set up so that at least one test group was presented with a high fraction of lethalities.

Castor Oil-Induced Diarrhea. Male Sprague-Dawley rats (350–400 g) were fasted overnight in hanging wire cages and allowed free access to water. A typical experiment involved 12 rats: 6 untreated controls and 6 pretreated with polyamine analogues (subcutaneous injection 30 minutes prior to castor oil). All animals were then challenged with castor oil (gastric gavage of 1 ml/200 g body weight) at T=0 and were monitored for a 6 hour period during which they received no food or water. The time of onset of diarrhea for the control rats was between 30 and 90 minutes and lasted for 6 hours. Time of diarrheal onset is recorded for each animal in the control and treated groups and the animal weight and stool weight is recorded at 2, 4 and 6 hour time points. The antidiarrheal activities of polyamine analogues was assessed at the following doses: DEHSPM—5 mg/kg, (HO)$_2$DEHSPM—5 mg/kg and DENSPM—40 mg/kg.

4,9-Dibenzyl-1,12-dichloro-2(S),11(S)-dihydroxy-4,9-diazadodecane (2). MgSO$_4$ (5 g) was added to a solution of 1 (5.45 g, 20.3 mmol) and (S)-(+)-epichlorohydrin (4.13 g, 44.7 mmol) in distilled methanol (120 ml). The reaction mixture was stirred at room temperature for 2 days until completion of the reaction as monitored by TLC. The solid was filtered and the filtrate was concentrated in vacuo to leave an oil. Flash chromatography with 80/15/5 hexane/EtOA/EtOH afforded 6.23 g (68%) of 2 as an oil: NMR δ 1.40 (m, 4 H), 2.50 (m, 8 H), 3.50 (m, 4 H), 3.56 (dd, 4 H, J=25.6 and 1.2), 3.80 (m, 2 H), 7.27 (m, 10 H). Anal. calcd. for C$_{24}$H$_{34}$Cl$_2$N$_2$O$_2$: C 63.57, H 7.56, N 6.18. Found: C 63.41, H 7.61, N 6.23.

4,9-Dibenzyl-1,12-dicyano-(R),11(R)-dihydroxy-4,9diazadodecane (3). A mixture of 2 (2.91 g, 6.4 mmol), KCN (4.18 g, 64 mmol) and 18-crown-6 (0.17 g, 0.64 mmol) in dry acetonitrile (80 ml) was heated at 60° C. for 2 days. The solid was filtered and solvent was removed by rotary evaporation. The residue was purified using flash column chromatography with 60/35/5 hexane/EtOAc/EtOH to afford a solid which was recrystallized from 30/70 $CH_2C_2$/hexane to furnish 1.8 g (65%) of 3 as a white solid: mp 85° C.; NMR δ 1.46 (m, 4 H), 2.48 (m, 12 H), 3.60 (dd, 4 H, J=24.2 and 4.5), 3.73 (m, 2 H), 7.29 (m, 10 H). Anal. calcd. for $C_{26}H_{34}N_4O_2$: C 71.86, H 7.89, N 12.89. Found: C 71.78, H 7.95, N 12.80.

$N^5,N^{10}$-Dibenzyl-3(R),12(R)-dihydroxyhomospermine (4). W-2 grade Raney nickel (0.7 g) was added to a solution of 3 (1.42 g, 3.04 mmol) in methanol (100 ml) in a 500 ml Parr bottle and a slow stream of $NH_3$ was bubbled through the mixture for 20 minutes at 0° C. Hydrogenation was carried out with shaking at 50 psi for 7 hours. The suspension was filtered through Celite, and the solvents were evaporated in vacuo to afford 1.12 g (86%) of 4 as an oil: NMR δ 1.41 (m, 4 H), 2.42 (m, 8 H), 2.82 (m, 8 H), 3.55 (d, 4 H, J=2.6), 3.71 (m, 2 H), 7.52 (m, 10 H). HRMS calcd. for $C_{26}H_{43}N_4O_2$: 443.3386 (M+1). Found: 443.3383 (M+1).

3(R),12(R) -Diacetoxy-$N^1,N^{14}$-diacetyl-$N^5N,^{10}$-dibenzylhomospermine (5). A solution of 4 (2.4 g, 5.42 mmol) in $CH_2Cl_2$ (100 ml) was treated with acetic anhydride (10 ml) at room temperature for 3 hours. The volatiles were evaporated in vacuo and the concentrate was purified by flash chromatography with 65/25/15 hexane/EtOAc/EtOH to give 2.39 g (73%) of 5 as an oil: NMR δ 1.44 (m, 4 H), 1.96 (m, 3 H), 1.98 (m, 4 H), 2.07 (s, 3 H), 2.46 (m, 8 H), 2.57 (m, 2 H), 3.02 (m, 2 H), 3.42 (m, 2 H), 3,59 (m, 4 H), 7.28 (m, 10 H). Anal. calcd. for $C_{34}H_{50}N_4O_6$: C 66.86, H 8.25, N 9.17. Found: C 66.81, H 8.22, N 9.16.

$N^5,N^{10}$-Dibenzyl-$N^1N^{14}$-diethyl-3(R),12(R)-dihydroxyhomospermine (6). $LiAlH_4$ (1 m in THF, 15 ml, 15 mmol) was added to a solution of 5 (1.73 g, 2.83 mmol) in dry THF (50 ml). The mixture was stirred at 65° C. for 3 hours under $N_2$. The reaction was cautiously quenched with water (5 ml), followed by filtration of solids. Evaporation of the filtrate and flash chromatography on silica gel, eluting with 5% concentration $NH_4OH$ in methanol, produced 0.6 g (44%) of 5 as an oil: NMR δ 1.09 (m, 6 H), 1.47 (m, 8 H), 2.64 (m, 16 H), 3.59 (m, 4 H), 3.75 (m, 2 H), 7.28 (m, 10 H). Anal. calcd. for $C_{30}H_{50}N_4O_2$: C 72.25, H 10.10, N 11.23. Found: C 72.31, H 10.07, N 11.15.

$N^1,N^{14}$-Diethyl-3(R),12(R)-dihydroxyhomospermine tetrahydrochloride [$(HO)_2$DEHSPM] (7). Pd on C (10%, 0.4 g) was added to a solution of 6 (2.26 g, 4.53 mmol) in concentrated HCl (3 ml) and EtOH (100 ml) and the suspension was degassed three times with $N_2$. After stirring under hydrogen (1 atm, 3 hours), the catalyst was filtered off and washed with water (10 ml). The solvents were removed under reduced pressure to give a white solid. Recrystallization from aqueous EtOH gave 1.5 g (725) of 7 as a crystalline solid: NMR ($D_2O$) δ 1.07 (t, 6 H, J=2.4), 1.60 (m, 4 H), 1.74 (m, 4 H), 2.91 (m, 16 H), 3.84 (m, 2 H). Anal. calcd. for $C_{16}H_{42}Cl_4N_4O_2$: C 41.39, H 9.12, N 12.07. Found: C 41.51, H 9.06, N, 12.00.

3(R),12(R)-Dihydroxyhomosperminetetrahydrochloride [$(HO)_2$HSPM] (8). HCl (1N, 10 ml) and 10% Pd/C (0.08 g) were added to a solution of 4 (0.764 g, 1.73 mmol) in methanol (100 ml) and the suspension was flushed three times with nitrogen. The mixture was exposed to hydrogen for 3 hours at atmospheric pressure followed by filtration of catalyst on Celite. The filtrate was evaporated in vacuum to give a white solid which was recrystallized from aqueous ethanol to produce 0.56 g (80%) of 8 as a crystalline solid: NMR ($D_2O$) δ 1.63 (m, 8 H), 2.97 (m, 12 H), 3.92 (m, 2 H). Anal. calcd. for $C_{12}H_{34}Cl_4N_4O_2$: C 35.31, H 8.39, N 13.72. Found: C 35.60, H 8.22, N 13.60.

I claim:
1. A polyamine having the formula:

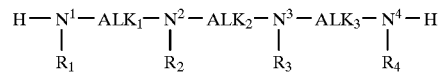

or its possible stereoisomers or a salt thereof with a pharmaceutically acceptable acid wherein:

$R_1$ and $R_4$ may be the same or different and are alkyl, aryl, aryl alkyl or cycloalkyl, optionally having an alkyl chain interrupted by at least one etheric oxygen atom;

$R_2$ and $R_3$ may be the same or different and are $R_1$, $R_4$ or H;

$N^1$, $N^2$, $N^3$ and $N^4$ are nitrogen atoms capable of protonation at physiological pH's;

$ALK_1$, $ALK_2$ AND $ALK_3$ may be the same or different and are straight or branched chain alkylene bridging groups having 1 to 4 carbon atoms which effectively maintain the distance between the nitrogen atoms such that the polyamine:

(i) is capable of uptake by a target cell upon administration of the polyamine to a human or non-human animal or is capable of binding to at least one polyamine site of a receptor located within or on the surface of a cell upon administration of the polyamine to a human or non-human animal; and (ii) upon uptake by the target cell, competitively binds via an electrostatic interaction between the positively charged nitrogen atoms to biological counter-anions;

the polyamine, upon binding to the biological counter-anion in the cell, functions in a manner biologically different than the intracellular polyamines; and further wherein at least one of said bridging groups $ALK_1$, $ALK_2$ and $ALK_3$ contains at least one —CH(OH)— group which is not alpha- to either of the nitrogen atoms.

2. A polyamine of claim 1 having the formula:

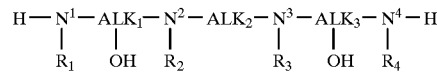

3. A polyamine of claim 2 having the formula:

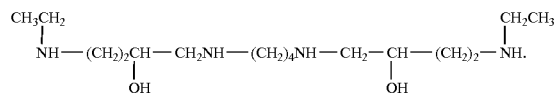

4. A pharmaceutical composition comprising an antineoplastic effective amount of a polyamine of claim 1 or a salt thereof with a pharmaceutically acceptable acid and a pharmaceutically acceptable carrier therefor.

5. A pharmaceutical composition comprising an anti-diarrheal effective amount of a polyamine of claim 1 or a salt thereof with a pharmaceutically acceptable acid and a pharmaceutically acceptable carrier therefor.

6. A method of treating diarrhea a human or non-human animal in need thereof comprising administering thereto an anti-diarrheal effective amount of a polyamine of claim 1 or a salt thereof with a pharmaceutically acceptable acid.

7. A method of treating a neoplasm in a human or non-human animal in need thereof comprising administering thereto an anti-neoplastic effective amount of a polyamine of claim 1 or a salt thereof with a pharmaceutically acceptable acid.

* * * * *

UNITED STATES PATENT AND TRADEMARK OFFICE
CERTIFICATE OF CORRECTION

PATENT NO. : 5,962,533
DATED : October 5, 1999
INVENTOR(S) : Raymond J. BERGERON, Jr.

It is certified that error appears in the above-identified patent and that said Letters Patent is hereby corrected as shown below:

In column 25, line 7 [claim 6, line 1]: after "diarrhea" insert -- in --

Signed and Sealed this

Sixteenth Day of January, 2001

Attest:

Q. TODD DICKINSON

Attesting Officer

Commissioner of Patents and Trademarks

UNITED STATES PATENT AND TRADEMARK OFFICE
CERTIFICATE OF CORRECTION

PATENT NO.   : 5,962,533
DATED        : October 5, 1999
INVENTOR(S)  : Raymond J. Bergeron, Jr.

It is certified that error appears in the above-identified patent and that said Letters Patent is hereby corrected as shown below:

Column 1,
Line 59, "The role of methylene backbone in" should read -- "Role of the methylene backbone in --.

Column 2,
Line 46, "and inhibitor" should be changed to read -- an inhibotor --.

Column 4,
Lines 1-37, in the Summary of the Invention", the formula and accompanying description should line up with what was presented in the Abstract and claims.

Column 5,
Line 1, "µm" should be changed to -- µM --.
Line 5, "µm" should be changed to -- µM --.
Line 12, "nm" should be changed to -- nM --.

Column 7,
The Table 1 column header "$K_i$ (µm)" should read -- $K_i$ (µM) --.

Column 8,
The Table 1 column header "$K_i$ (µm)" should read -- $K_i$ (µM) --.

Column 9,
The Table 1 column header "$K_i$ (µm)" should read -- Ki (µM) --.

Column 10,
The Table 1 column header "$K_i$ (µm)" should read -- $K_i$ (µM) --.

Column 11,
The Table 1 column header "$K_i$ (µm)" should read -- $K_i$ (µM) --.

Column 12,
The Table 1 column header "$K_i$ (µm)" should read -- $K_i$ (µM) --.

Column 13,
Line 8, "µm" should be changed to -- µM --.

UNITED STATES PATENT AND TRADEMARK OFFICE
CERTIFICATE OF CORRECTION

PATENT NO.    : 5,962,533
DATED         : October 5, 1999
INVENTOR(S)   : Raymond J. Bergeron, Jr.

It is certified that error appears in the above-identified patent and that said Letters Patent is hereby corrected as shown below:

Table 3,
Column header "$IC_{50}(\mu m)$ should rad -- $IC_{50}(\mu M)$ --.
Column header "$K_i^a(\mu m)$" should read -- $K_i^a(\mu M)$ --.

Column 14,
Line 34, "μm" should be changed to -- μM --.
Line 58, "μm" should read -- μM --.
Line 60, "μm" should read -- μM --.
Line 62, "μm" should read -- μM --.
Line 65, "μm" should read -- nM --.

Column 15,
Table 4, column header "Concentration (μm) should read -- Concentration (μM) --.
Line 28, "Concentration (μm) should read -- Concentration (μM) --.
Line 29, "Concentration (μm) should read -- Concentration (μM) --.
line 30, "Concentration (μm) should read -- Concentration (μM) --.

Column 17,
Line 42, "kg/mg" should be changed to -- mg/kg --.

Column 18,
Line 3, "mm" should be changed to -- mM --.

Column 19,
Line 37, "tetraamines's" should be changed to --tetraamines' --.

Column 20,
Line 5, change "Van der Walls" to -- Van der Waals --.

Column 21,
Line 11, "μm" should be changed to -- μM --.
Line 12, "μm" should be changed to -- μM --.
Line 16, "nm" should be changed to -- nm --.
Line 46, "mm" should be changed to -- mM --.
Line 48, "μm" should be changed to -- μM --.
Line 48, "mm" should be changed to -- mM --.
Line 49, "μm" should be changed to -- μM --.

UNITED STATES PATENT AND TRADEMARK OFFICE
CERTIFICATE OF CORRECTION

PATENT NO.   : 5,962,533
DATED        : October 5, 1999
INVENTOR(S)  : Raymond J. Bergeron, Jr.

It is certified that error appears in the above-identified patent and that said Letters Patent is hereby corrected as shown below:

Column 21 contd
Line 51, "µm" should be changed to -- µM --.
Line 52, "µm" should be changed to --µM --.

Column 22,
Line 60, "EtOA" should read -- EtOAc --.

Column 23,
Line 5, "30/70 $CH_2C_2$/hexane" should read -- 30/70 $CH_2Cl_2$/hexane --.
Line 56, "(725)" should read -- (72%) --.

Signed and Sealed this

Thirty-first Day of July, 2001

*Attest:*

*Attesting Officer*

NICHOLAS P. GODICI
*Acting Director of the United States Patent and Trademark Office*